(12) United States Patent
Vogelstein et al.

(10) Patent No.: US 9,976,184 B2
(45) Date of Patent: May 22, 2018

(54) MUTATIONS IN PANCREATIC NEOPLASMS

(75) Inventors: Bert Vogelstein, Baltimore, MD (US); Kenneth W. Kinzler, Baltimore, MD (US); Jian Wu, Baltimore, MD (US); Luis Diaz, Ellicott City, MD (US); Nickolas Papadopoulos, Towson, MD (US); Hanno Matthaei, Bonn (DE); Ralph Hruban, Baltimore, MD (US); Anirban Maitra, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days. days.

(21) Appl. No.: 14/128,478

(22) PCT Filed: Jun. 22, 2012

(86) PCT No.: PCT/US2012/043783
§ 371 (c)(1),
(2), (4) Date: Feb. 11, 2014

(87) PCT Pub. No.: WO2012/178034
PCT Pub. Date: Dec. 27, 2012

(65) Prior Publication Data
US 2014/0179538 A1   Jun. 26, 2014

Related U.S. Application Data

(60) Provisional application No. 61/500,479, filed on Jun. 23, 2011.

(51) Int. Cl.
*C12Q 1/68* (2018.01)
*C12P 19/34* (2006.01)

(52) U.S. Cl.
CPC ...... *C12Q 1/6886* (2013.01); *C12Q 2600/112* (2013.01); *C12Q 2600/156* (2013.01)

(58) Field of Classification Search
CPC ............ C12Q 1/6806; C12Q 2535/122; C12Q 1/6886; C12Q 2600/112; C12Q 2600/156
See application file for complete search history.

(56) References Cited

U.S. PATENT DOCUMENTS

2006/0088870 A1   4/2006   Finkelstein et al.
2006/0147936 A1   7/2006   Frey et al.
2010/0190970 A1   7/2010   Slack et al.

FOREIGN PATENT DOCUMENTS

WO   2011031560 A2   3/2011
WO   2013074438 A1   5/2013

OTHER PUBLICATIONS

Jones S. et al. Science (Apr. 10, 2009) vol. 324, p. 217.*
Khalid A. et al. vol. 69, No. 6 : 2009 Gastrointestinal Endoscopy 1095-1102.*
Fredha P.U. et al. Pituitary. 2007;10(3):275-82.*
Pennisi E. Science; Sep 18, 1998; 281, 5384, p. 1787-1789.*
Lucentini J. The Scientist, Dec. 20, 2004, p. 20.*
Hegele R. A. et al. Arterioscler Thromb Vasc Biol. 2002;22:1058-1061.*
Imanaka M. et al., Internal Medicine, vol. 46 (2007) No. 18 pp. 1577-1583.*
Kan, Z. et al., Nature (2010) vol. 466, pp. 869-873, inlcudes 2 additional pritned pages of methods, and online supplemntary tables and figures.*
Weinstein L.S. et al. NEJM (1991) p. 1688-1695.*
Pitman M.B. et al. Cancer Cytopathology Feb. 25, 2010, 1-13.*
Furukawa, T. et al., 'Whole-exome sequencing uncovers frequent GNAS mutations in intraductal papillary mucinous neoplasms of the pancreas' ,Sci Rep., Nov. 18, 2011, vol. 1, No. 161, doi:10.1038/srep00161. see Abstract.
Wilson, CH. et al., 'The activating mutation R201C in GNAS promotes intestinal tumourigenesis in ApcMin/+ mice via activation of Wnt and ERK1/2 MAPK pathways' , Oncogene, Aug. 12, 2010, vol. 29, No. 32, pp. 4567-4575. see Abstract.
Wu, J. et al., 'Recurrent GNAS mutations define an unexpected pathway for pancreatic cyst development' , Sci Transl Med., Jul. 20, 2011, vol. 3, No. 92, 92ra66. doi:10.1126/scitranslmed.3002543. see Abstract.
International Search Report dated Dec. 27, 2012, for PCT/US2012/043783.
Extended European Search Report issued in related European Application No. 12802288.6, dated Jan. 16, 2015.
Al-Haddad et al., "The safety of fine-needle aspiration guided by endoscopic ultrasound: a prospective study," *Endoscopy* 40, 204-208 (2008).
Khalid et al., "Pancreatic cyst fluid DNA analysis in evaluating pancreatic cysts: a report of the PANDA study," *Gastrointest Enclose* 69, 1095-1102 (2009).
Parmigiani et al., "Design and analysis issues in genome-wide somatic mutation studies of cancer," *Genomics* 93, 17-21 (2009).
Schoedel et al., "K-Ras and microsatellite marker analysis of fine-needle aspirates from intraductal papillary mucinous neoplasms of the pancreas," *Diagnostic Cytopathology* 34, 605-608 (2006).
Allen et al., "Pancreatic Cyst Fluid Protein Expression Profiling for Discriminating Between Serous Cystadenoma and Intraductal Papillary Mucinous Neoplasm," *Annals of Surgery* 250, 754-760 (2009).
Almoguera et al., "Most human carcinomas of the exocrine pancreas contain mutant c-K-ras genes," *Cell* 53. 549-554 (1988).

(Continued)

*Primary Examiner* — Stephen T Kapushoc
(74) *Attorney, Agent, or Firm* — Fish & Richardson P.C.

(57) ABSTRACT

To help reveal the pathogenesis of these lesions, we purified the DNA from Intraductal Papillary Mucinous Neoplasm (IPMN) cyst fluids from 19 patients and searched for mutations in 169 genes commonly altered in human cancers. We identified recurrent mutations at codon 201 of GNAS. We found that GNAS mutations were present in 66% of IPMNs and that either KRAS or GNAS mutations could be identified in 96%. In eight cases, we could investigate invasive adenocarcinomas that developed in association with IPMNs containing GNAS mutations. In seven of these eight cases, the GNAS mutations present in the IPMNs were also found in the invasive lesion. GNAS mutations were not found in other types of cystic neoplasms of the pancreas or in invasive adenocarcinomas not associated with IPMNs. These data suggest that GNAS mutations can inform the diagnosis and management of patients with cystic pancreatic lesions.

22 Claims, 30 Drawing Sheets

(56) References Cited

OTHER PUBLICATIONS

Bartsch et al., "K-ras oncogene mutations indicate malignancy in cystic tumors of the pancreas," *Ann Surg* 228, 79-86 (1998).

Correa-Gallego et al., "Incidental Pancreatic Cysts: Do We Really Know What We Are Watching?" *Pancreatology* 10, 144-150 (2010).

Crippa et al., "Mucin-Producing Neoplasms of the Pancreas: An Analysis of Distinguishing Clinical and Epidemiologic Characteristics," *Clinical Gastroenterology and Hepatology* 8, 213-219.e214 (2010).

Dahabreh et al., "Systematic review: Antiepidermal growth factor receptor treatment effect modification by KRAS mutations in advanced colorectal cancer." *Ann Intern Med* 154, 37-49 (2011).

De Jong et al., "High Prevalence of Pancreatic Cysts Detected by Screening Magnetic Resonance Imaging Examinations," *Clinical Gastroenterology and Hepatology* 8, 806-811 (2010).

Diaz et al., "McCune-Albright syndrome and disorders due to activating mutations of GNAS1," *J Pediatr Endocrinol Metab* 20, 853-880 (2007).

Diehl et al., "Circulating mutant DNA to assess tumor dynamics." *Nat Med* 14, 985-990 (2008).

Diehl et al., "BEAMing: singlemolecule PCR on microparticles in water-in-oil emulsions," *Nature Methods* 3, 551-559 (2006).

Dong et al., "Detecting Colorectal Cancer in Stool with the Use of Multiple Genetic Targets," *J Natl Cancer Inst* 93, 858-865. (2001).

Fouquet et al., "Rapid stud sensitive p53 alteration analysis in biopsies from lung cancer patients using a functional assay and a universal oligonucleotide array: a prospective study," *Clin Cancer Res* 10, 3479-3489 (2004).

Fragoso et al., "Activating mutation of the stimulatory G protein (gsp) as a putative cause of ovarian and testicular human stromal Leydig cell tumors," *J Clin Endocrinol Metab* 83, 2074-2078 (1998).

Freda et al., "Analysis of GNAS mutations in 60 growth hormone secreting pituitary tumors: correlation with clinical and pathological characteristics and surgical outcome based on highly sensitive GH and IGF-I criteria for remission," *Pituitary* 10, 275-282 (2007).

Fritz et al., "Global Genomic Analysis of Intraductal Papillary Mucinous Neoplasms of the Pancreas Reveals Significant Molecular Differences Compared to Ductal Adenocarcinoma," *Annals of Surgery* 249, 440-447 (2009).

Fujii et al., "Genetic progression and heterogeneity in intraductal papillary-mucinous neoplasms of the Pancreas," *American Journal Pathology* 151, 8 (1997).

Furukawa et al., "Classification of types of intraductal papillary-mucinous neoplasm of the pancreas: a consensus study." *Virchows Arch* 447, 794-799 (2005).

Herman et al., "Filter-based hybridization capture of subgenomes enables resequencing and copy-number detection," *Nature Methods* 6, 507-510 (2009).

Hong et al., "Multiple genes are hypermethylated in intraductal papillary mucinous neoplasms of the pancreas, " *Mod Pathol* 21, 9 (2008).

Idziaszczyk et al., "Analysis of the frequency of GNAS codon 201 mutations in advanced colorectal cancer," *Cancer Genetics and Cytogenetics* 202, 67-69 (2010).

Izawa et al., "Clonality and Field Cancerization in Intraductal Papillary-Mucinous Tumors of the Pancreas," *Cancer* 92, 11 (2001).

Jones et al., "Comparative lesion sequencing provides insights into tumor evolution," *Proc Natl Acad Sci USA* 105, 4283-4288 (2008).

Jones et al., "Core Signaling Pathways in Human Pancreatic Cancers Revealed by Global Genomic Analyses," *Science* 321, 1801-1806 (2008).

Kalfa et al., "Activating Mutations of the Stimulatory G Protein in Juvenile Ovarian Granulosa Cell Tumors: A New Prognostic Factor?" *Journal of Clinical Endocrinology & Metabolism* 91, 1842-1847 (2006).

Katz et al., "Diagnosis and Management of Cystic Neoplasms of the Pancreas: An Evidence Based Approach," *Journal of the American College of Surgeons* 207, 106-120 (2008).

Ke et al., "Proteontic Analyses of Pancreatic Cyst Fluids," *Pancreas* 38, 10 (2009).

Kimura et al., "Analysis of small cystic lesion of the pancreas," *Int J Pancreatol* 18, 197-206 (1995).

Kitago et al., "Comparison of K-ras point mutation distributions in intraductal papillarymucinous tumors and ductal adenocarcinoma of the pancreas," *International Journal of Cancer* 110, 177-182 (2004).

Kloppel et al., "Cystic Lesions and Neoplasms of the Pancreas," *Pancreatology* 1, 8 (2001).

Laffan et al., "Prevalence of unsuspected pancreatic cysts on MDCT," *AJR Am J Roentgenol* 191, 802-807 (2008).

Lania et al., "G-protein and signalling in pituitary tumours," *Horm Res* 71 Suppl 2, 95-100 (2009).

Lania et al., "Mechanisms of disease: Mutations of G proteins and G-protein-coupled receptors in endocrine diseases," *Nat Clin Pract Endocrinol Metab* 2, 681-693 (2006).

Lee et al., "Prevalence of incidental pancreatic cysts in the adult population on MR imaging," *Am J Gastroenterol* 105, 2079-2084 (2010).

Luo et al., "Improving the fidelity of Thermus thermophilus DNA ligase," *Nucleic Acids Res* 24, 3071-3078 (1996).

Matthaei et al., "Cystic precursors to invasive pancreatic cancer," *Nature Reviews Gastroenterology & Hepatology* 8, 141-150 (2011).

Poultsides et al., "Histopathologic basis for the favorable survival after resection of intraductal papillary mucinous neoplasm-associated invasive adenocarcinoma of the pancreas," *Ann Surg* 251, 470-476 (2010).

Rago et al., "Serial Assessment of Human Tumor Burdens in Mice by the Analysis of Circulating DNA," *Cancer Res* 67, 9364-9370 (2007).

Sahani et al., "Cystic pancreatic lesions: a simple imaging-based classification system for guiding management" *Radiographies* 25, 1471-1484 (2005).

Salvia et al., "Main-duct intraductal papillary mucinous neoplasms of the pancreas: clinical predictors of malignancy and long-term survival following resection," *Ann Surg* 239, 678-685; discussion 685-677 (2004).

Sawhney et al., "Comparison of carcinoembryonic antigen and molecular analysis in pancreatic cyst fluid," *Gastrointestinal Endoscopy* 69, 1106-1110 (2009).

Schonleben et al., "BRAF and KRAS gene mutations in intraductal papillary mucinous neoplasm/carcinoma (IPMN/IPMC) of the pancreas," *Cancer Letters* 249, 242-248 (2007).

Schonleben et al., "Mutational analyses of multiple oncogenic pathways in intraductal papillary mucinous neoplasms of the pancreas," *Pancreas* 36, 168-172 (2008).

Sin et at. "LigAmp for sensitive detection of singlenucleotide differences," *Nat Methods* 1 141-147 (2004).

Shibata et al., "Genetic Heterogeneity of the c-Kras locus in colorectal adenomas but not in adenocarcinomas," *J Natl Cancer Inst* 85, 1058-1063 (1993).

Shin et al., "PEComa of the retroperitoneum" *Pathology* 40, 93-95 (2008).

Sohn et al., "Intraductal papillary mucinous neoplasms of the pancreas: an updated experience," *Ann Surg* 239, 788-797; discussion 797-789 (2004).

Sohn et al., "Resected adenocarcinoma of the pancreas 616 patients results, outcomes, and prognostic indicators;" *Journal of Gastrointestinal Surgery* 4, 13 (2000).

Soldini et al., "Progressive genomic alterations in intradctal papillary mucinous tumours of the pancreas and morphologically similar lesions of the pancreatic ducts," *The Journal of Pathology* 199, 453-461 (2003).

Tanaka et al., "Controversies in the management of pancreatic IPMN," *Nature Reviews Gastroenterology & Hepatology* 8, 56-60 (2011).

Tanaka et al., "International consensus guidelines for management of intraductal papillary mucinous neoplasms and mucinous cystic neoplasms of the pancreas," *Pancreatology* 6, 17-32 (2006).

Taouli et al., "Intraductal Papillary Mucinous Tumors of the Pancreas: Helical CT with Histopathologic Correlation," *Radiology* 217, 8 (2000).

(56) References Cited

OTHER PUBLICATIONS

Tseng et al., "Serous Cystadenoma of the Pancreas, Tumor Growth Rates and Recommendations for Treatment," *Annals of Surgery* 242 3:413-421 (2005).

Wada et al., Does "clonal progression" relate to the development of intraductal papillary mucinous tumors of the pancreas? *Journal of Gastrointestinal Surgery* 8, 289-296 (2004).

Wood et al., "The Genomic Landscapes of Human Breast and Colorectal Cancers," *Science* 318, 1108-1113 (2007).

Yamasaki et al., "GH-secreting pituitary adenomas infrequently contain inactivating mutations of PRKAR1A and LOH of 17q23-24," *Clin Endocrinol (Oxf)* 58, 464-470 (2003).

* cited by examiner

Fig. 5

Table S1. Genes analyzed by massively parallel sequencing in IPMN cyst fluids.

| Gene symbol | Accession Number | Oncogene or Tumor Suppressor Gene |
|---|---|---|
| ABL1 | X16416 | Oncogene |
| ARHGAP29 | NM_004815.2 | Suppressor Gene |
| AKT1 | NM_005163 | Oncogene |
| ALK | NM_004304 | Oncogene |
| JARID1C | NM_004187.1 | Suppressor Gene |
| APC | NM_000038 | Suppressor Gene |
| ATM | NM_000051 | Suppressor Gene |
| UBR4 | NM_020765.1 | Suppressor Gene |
| BRAF | NM_004333 | Oncogene |
| BRCA1 | NM_007294.1 | Suppressor Gene |
| BRCA2 | NM_000059.1 | Suppressor Gene |
| CBL | NM_005188.1 | Oncogene |
| CDC73 | NM_024529.3 | Suppressor Gene |
| CDH1 | NM_004360.2 | Suppressor Gene |
| CDKN2A | NM_000077 | Suppressor Gene |
| CEBPA | NM_004364.2 | Suppressor Gene |
| CSF1R | NM_005211 | Oncogene |
| CTNNA1 | NM_001903.2 | Suppressor Gene |
| CTNNB1 | NM_001904 | Oncogene |
| ATR | NM_001184 | Suppressor Gene |
| CYLD | NM_015247.1 | Suppressor Gene |
| LRRK2 | SU_LRRK2 | Suppressor Gene |
| KIAA1409 | ENST00000256339 | Suppressor Gene |
| SPTAN1 | ENST00000372731 | Suppressor Gene |
| ATRX | NM_138271.1 | Suppressor Gene |
| SPEG | SU_SPEG | Suppressor Gene |
| MAST4 | SU_MAST4 | Suppressor Gene |
| DPYSL4 | ENST00000338492 | Oncogene |
| EGFL6 | NM_015507.2 | Oncogene |
| EGFR | NM_005228 | Oncogene |
| WNK2 | SU_WNK2 | Suppressor Gene |
| CAD | NM_004341.2 | Suppressor Gene |
| SORL1 | ENST00000260197 | Suppressor Gene |
| NUP214 | NM_005085.2 | Suppressor Gene |
| ERBB2 | NM_004448 | Oncogene |
| TECTA | ENST00000392793 | Suppressor Gene |
| ADAMTS20 | NM_025003.2 | Suppressor Gene |
| TRIP11 | ENST00000267622 | Suppressor Gene |
| FAM123B | NM_152424.1 | Suppressor Gene |
| FBXW7 | NM_033632.1 | Suppressor Gene |
| TAF1 | NM_138923 | Suppressor Gene |
| FGFR3 | NM_000142 | Oncogene |
| FLT3 | Z26652 | Oncogene |

FROM FIG. 5

| | | |
|---|---|---|
| COL14A1 | NM_021110.1 | Suppressor Gene |
| FOXL2 | NM_023067.2 | Oncogene |
| NUP98 | NM_016320.2 | Suppressor Gene |
| GATA1 | NM_002049.2 | Suppressor Gene |
| CDC42BPB | NM_006035 | Suppressor Gene |
| LTBP1 | NM_206943.1 | Suppressor Gene |
| TAF1L | NM_153809 | Suppressor Gene |
| GNAQ | NM_002072.2 | Oncogene |
| GNAS | NM_000516.3 | Oncogene |
| ITSN2 | NM_006277.1 | Suppressor Gene |
| N4BP2 | NM_018177.2 | Suppressor Gene |
| JARID1A | NM_005056.1 | Suppressor Gene |
| DEPDC2 | NM_024870.2 | Suppressor Gene |
| HNF1A | NM_000545.3 | Suppressor Gene |
| HRAS | NM_005343 | Oncogene |
| IDH1 | NM_005896.2 | Oncogene |
| IDH2 | NM_002168.2 | Oncogene |
| GLI3 | NM_000168.2 | Suppressor Gene |
| CENTD3 | NM_022481.4 | Suppressor Gene |
| BAZ1A | NM_013448.2 | Suppressor Gene |
| MAP4K4 | NM_145686 | Suppressor Gene |
| COL1A1 | ENST00000225964 | Suppressor Gene |
| ASXL1 | ENST00000358956 | Suppressor Gene |
| JAK2 | NM_004972 | Oncogene |
| JAK3 | NM_000215 | Oncogene |
| ROCK2 | NM_004850 | Suppressor Gene |
| ROCK1 | NM_005406 | Suppressor Gene |
| IKBKAP | NM_003640.2 | Suppressor Gene |
| KIT | NM_000222 | Oncogene |
| IGF1R | NM_000875 | Suppressor Gene |
| KRAS | NM_004985 | Oncogene |
| STK36 | NM_015690 | Suppressor Gene |
| RAD50 | NM_133482.1 | Suppressor Gene |
| MAP3K6 | NM_004672 | Suppressor Gene |
| PER1 | ENST00000317276 | Suppressor Gene |
| WNK4 | NM_032387 | Suppressor Gene |
| MAP2K4 | NM_003010 | Suppressor Gene |
| ADAMTS18 | NM_199355.1 | Suppressor Gene |
| MGA | XM_031689.7 | Suppressor Gene |
| ABL2 | NM_005158 | Suppressor Gene |
| TSC1 | NM_000368.2 | Suppressor Gene |

FROM FIG. 5 CONTINUE

| | | |
|---|---|---|
| MEN1 | ENST00000312049 | Suppressor Gene |
| MET | NM_000245 | Oncogene |
| TNKS2 | AF264912.1 | Suppressor Gene |
| TNK2 | NM_005781 | Suppressor Gene |
| TRIM33 | NM_015906 | Suppressor Gene |
| MLH1 | NM_000249.2 | Suppressor Gene |
| ULK2 | NM_014683 | Suppressor Gene |
| GUCY2F | NM_001522 | Suppressor Gene |
| HDAC4 | NM_006037.2 | Suppressor Gene |
| MPL | NM_005373.1 | Oncogene |
| MSH2 | NM_000251.1 | Suppressor Gene |
| MSH6 | NM_000179.1 | Suppressor Gene |
| ERN2 | NM_033266.1 | Suppressor Gene |
| USP24 | XM_371254.3 | Suppressor Gene |
| NF1 | ENST00000358273 | Suppressor Gene |
| NF2 | NM_000268.2 | Suppressor Gene |
| NFKB1 | NM_003998.2 | Suppressor Gene |
| EPHB1 | NM_004441 | Suppressor Gene |
| NOTCH1 | NM_017617.2 | Suppressor Gene |
| NOTCH2 | NM_024408.2 | Suppressor Gene |
| NPM1 | NM_002520.4 | Suppressor Gene |
| NRAS | NM_002524 | Oncogene |
| PHF14 | NM_001007157.1 | Suppressor Gene |
| ROR2 | NM_004560 | Suppressor Gene |
| TNPO1 | NM_002270.2 | Suppressor Gene |
| PDGFRA | NM_006206 | Oncogene |
| AXL | NM_001699 | Suppressor Gene |
| PRKD2 | NM_016457 | Suppressor Gene |
| TTK | NM_003318 | Suppressor Gene |
| PIK3CA | NM_006218.1 | Oncogene |
| TNNI3K | NM_015978 | Suppressor Gene |
| PRKAR1A | NM_212472.1 | Suppressor Gene |
| VEPH1 | ENST00000392832 | Suppressor Gene |
| HIF1A | NM_001530.2 | Suppressor Gene |
| PTCH1 | NM_000264.2 | Suppressor Gene |
| PTEN | NM_000314.4 | Suppressor Gene |
| PTPN11 | NM_002834.3 | Oncogene |
| PTPRC | NM_002838.2 | Oncogene |
| RPS6KA2 | NM_021135 | Suppressor Gene |
| BRD2 | NM_005104 | Suppressor Gene |
| ITGB3 | NM_000212.2 | Suppressor Gene |

FROM FIG. 5 CONTINUE

| Gene | Accession | Type |
|---|---|---|
| RB1 | NM_000321 | Suppressor Gene |
| RET | NM_020975 | Oncogene |
| ADAM29 | NM_014269.2 | Suppressor Gene |
| ANAPC5 | NM_016237.3 | Suppressor Gene |
| ITGB2 | NM_000211.1 | Suppressor Gene |
| CHUK | NM_001278 | Suppressor Gene |
| TCF12 | NM_207037.1 | Suppressor Gene |
| PDZRN4 | NM_013377.2 | Suppressor Gene |
| RUNX1 | ENST00000300305 | Suppressor Gene |
| SETD2 | ENST00000330022 | Suppressor Gene |
| SMAD2 | NM_005901.3 | Suppressor Gene |
| SMAD4 | NM_005359.3 | Suppressor Gene |
| SMARCA4 | NM_003072.2 | Suppressor Gene |
| SMARCB1 | NM_003073.2 | Suppressor Gene |
| PAK7 | NM_020341 | Suppressor Gene |
| SMO | NM_005631.3 | Oncogene |
| APBB1IP | NM_019043.3 | Suppressor Gene |
| SOCS1 | NM_003745.1 | Suppressor Gene |
| PRKCA | NM_002737 | Suppressor Gene |
| NEK11 | NM_024800.2 | Suppressor Gene |
| TCF7L2 | ENST00000369397 | Suppressor Gene |
| STK11 | NM_000455 | Suppressor Gene |
| ITK | NM_005546 | Suppressor Gene |
| MAP3K2 | NM_006609 | Suppressor Gene |
| ACVR1B | NM_020328 | Suppressor Gene |
| CDC7 | NM_003503.2 | Suppressor Gene |
| TGFBR2 | NM_003242 | Suppressor Gene |
| SRC | NM_005417 | Suppressor Gene |
| TNFAIP3 | NM_006290.2 | Suppressor Gene |
| BMPR1A | NM_004329 | Suppressor Gene |
| ACVR2A | NM_001616 | Suppressor Gene |
| RAD18 | NM_020165.2 | Suppressor Gene |
| SUFU | NM_016169.2 | Suppressor Gene |
| TP53 | NM_000546 | Suppressor Gene |
| MAP2K7 | NM_005043 | Suppressor Gene |
| STK32B | NM_018401 | Suppressor Gene |
| TSHR | NM_000369.1 | Oncogene |
| MGC42105 | NM_153361 | Suppressor Gene |
| STK19 | NM_032454 | Suppressor Gene |
| UTX | NM_021140.1 | Suppressor Gene |
| VHL | NM_000551.2 | Suppressor Gene |
| LDHB | NM_002300.3 | Suppressor Gene |
| WT1 | NM_024426.2 | Suppressor Gene |
| PHOX2B | ENST00000381741 | Suppressor Gene |

FIG. 5 CONTINUE

Table S2 - Characteristics of patients with IPMNs analyzed in this study, including GNAS and KRAS mutation status.

| IPMN # | KRAS mutation | GNAS mutation | Age at surgery | Sex | History of smoking | Post-operative diagnosis |
|---|---|---|---|---|---|---|
| 1 | G12V | R201C | 71 | M | No | IPMN |
| 2 | G12D | R201H | 68 | M | unknown | IPMN |
| 3 | G12D | R201H | 69 | M | unknown | IPMN |
| 4 | G12R | R201H | 73 | F | unknown | IPMN |
| 5 | G12D & G12R | No mutation detected | 66 | F | No | IPMN |
| 6 | G12R | R201C | 63 | M | unknown | IPMN |
| 7 | No mutation detected | R201H | 64 | F | No | IPMN |
| 8 | G12V | No mutation detected | 80 | M | No | IPMN |
| 9 | G12V & G12D | R201C & R201H | 74 | M | No | IPMN |
| 10 | G12D | R201C | 39 | F | No | IPMN |
| 11 | G12D | R201C | 67 | F | No | IPMN |
| 12 | G12V | No mutation detected | 70 | M | No | IPMN |
| 13 | G12V | R201H | 78 | M | No | IPMN |
| 14 | G12V | R201H | 79 | M | No | IPMN |
| 15 | G12D | R201C | 84 | M | No | IPMN |
| 16 | G12D | R201C | 66 | F | No | IPMN |
| 17 | G12D | R201C | 63 | F | Yes | IPMN |
| 18 | G12D | R201C | 81 | F | Yes | IPMN |
| 19 | G12D | R201H | 69 | M | Yes | IPMN |
| 20 | G12V | R201C | 70 | M | unknown | IPMN |

| Cyst Grade | Cyst diameter (cm) | Duct type | IPMN :Subtype | Cyst location | Sample type |
|---|---|---|---|---|---|
| intermediate | 3.0 | mixed | gastric | body/tail | Cyst wall |
| high | 2.0 | branch | gastric | body/tail | Cyst wall |
| intermediate | 2.0 | branch | gastric | head | Cyst wall |
| high | 3.2 | main | pancreatobiliary | head | Cyst wall |
| intermediate | 4.0 | branch | gastric | entire pancreas | Cyst fluid |
| high | 8.0 | mixed | intestinal | head | Cyst wall |
| high | 2.0 | branch | intestinal | body/tail | Cyst wall |
| high | 2.0 | main | gastric | body/tail | Cyst wall |
| high | 6.5 | main | pancreatobiliary | entire pancreas | Cyst wall |
| low | 2.0 | branch | gastric | head | Cyst wall |
| low | 2.0 | main | gastric | head | Cyst wall |
| high | 2.0 | main | gastric | head | Cyst wall |
| high | 3.0 | branch | gastric | head | Cyst wall |
| high | 5.0 | branch | gastric | head | Cyst wall |
| low | 1.5 | branch | gastric | head | Cyst wall |
| intermediate | 1.8 | branch | gastric | body/tail | Cyst wall |
| high | 1.8 | branch | gastric | head | Cyst wall |
| intermediate | 3.0 | not determined | gastric | head | Cyst wall |
| low | 2.5 | not determined | gastric | head | Cyst wall |
| high | 5.0 | mixed | not determined | body/tail | Cyst wall |

| FROM FIG. 6 CONTINUE | | | | | TO FIG. 6 CONTINUE |
|---|---|---|---|---|---|
| 21 | No mutation detected | R201H | 80 | M | unknown | IPMN |
| 22 | No mutation detected | R201C | 50 | F | unknown | IPMN |
| 23 | No mutation detected | R201C | 81 | M | unknown | IPMN |
| 24 | G12V | R201C | 51 | F | unknown | IPMN |
| 25 | No mutation detected | R201H | 78 | M | unknown | IPMN |
| 26 | G12D | R201H | 70 | F | unknown | IPMN |
| 27 | G12D | R201C | 66 | F | unknown | IPMN |
| 28 | G12D | No mutation detected | 62 | M | unknown | IPMN |
| 29 | G12D & G12V | No mutation detected | 88 | M | Yes | IPMN |
| 30 | No mutation detected | R201C | 65 | M | Yes | IPMN |
| 31 | G12D & G12V & G12R | R201H | 79 | M | unknown | IPMN |
| 32 | G12R | No mutation detected | 74 | F | unknown | IPMN |
| 33 | G12V | R201H | 82 | F | unknown | IPMN |
| 34 | G12V | R201C | 75 | M | No | IPMN |
| 35 | G12V & G12D | R201H | 58 | F | No | IPMN |
| 36 | G12D | R201H | 69 | M | Yes | IPMN |
| 37 | G12V | No mutation detected | 73 | M | unknown | IPMN |
| 38 | No mutation detected | No mutation detected | 48 | M | No | IPMN |
| 39 | G12D | No mutation detected | 69 | F | Yes | IPMN |
| 40 | G12R | R201C | 76 | F | Yes | IPMN |
| 41 | G12D | R201C | 72 | M | Yes | IPMN |
| 42 | G12D | R201C | 68 | M | Yes | IPMN |

FIG. 6 CONTINUE

FROM FIG. 6 CONTINUE

| | | | | |
|---|---|---|---|---|
| high | 0.7 | main | gastric | body/tail | Cyst wall |
| low | 1.2 | mixed | intestinal | body/tail | Cyst wall |
| high | 2.5 | main | intestinal | body/tail | Cyst wall |
| intermediate | 1.0 | mixed | gastric | head | Cyst wall |
| high | 3.0 | mixed | intestinal | head | Cyst wall |
| intermediate | 1.4 | branch | not determined | head | Cyst wall |
| low | 2.7 | mixed | gastric | head | Cyst wall |
| intermediate | 3.5 | branch | gastric | head | Cyst wall |
| high | 3.5 | main | pancreatobiliary | body/tail | Cyst fluid |
| high | 6.5 | main | gastric | head | Cyst fluid |
| high | 2.5 | branch | not determined | head | Cyst fluid |
| high | 5.0 | mixed | pancreatobiliary | head | Cyst wall |
| high | 0.5 | main | not determined | body/tail | Cyst fluid |
| high | 2.8 | main | gastric | head | Cyst fluid |
| low | 1.5 | branch | gastric | head | Cyst fluid |
| intermediate | 2.8 | branch | gastric | body/tail | Cyst wall |
| intermediate | 2.0 | branch | not determined | head | Cyst fluid |
| high | 2.5 | main | not determined | head | Cyst fluid |
| low | 1.1 | mixed | not determined | head | Cyst fluid |
| low | 4.0 | branch | not determined | tail | Cyst fluid |
| intermediate | 1.9 | branch | not determined | head | Cyst fluid |
| high | 2.0 | mixed | not determined | head | Cyst fluid |

FROM FIG. 6 CONTINUE

|    |                      |                    |    |   |         |      |
|----|----------------------|--------------------|----|---|---------|------|
| 43 | G12D                 | R201H              | 76 | F | Yes     | IPMN |
| 44 | G12D                 | No mutation detected | 70 | F | No      | IPMN |
| 45 | No mutation detected | R201H              | 85 | F | No      | IPMN |
| 46 | No mutation detected | R201H              | 72 | F | No      | IPMN |
| 47 | G12D                 | No mutation detected | 62 | M | No      | IPMN |
| 48 | G12R                 | R201C & R201H      | 84 | F | No      | IPMN |
| 49 | G12D                 | No mutation detected | 71 | M | unknown | IPMN |
| 50 | G12D                 | R201C              | 70 | M | unknown | IPMN |
| 51 | G12V                 | No mutation detected | 76 | F | unknown | IPMN |
| 52 | G12V & G12R          | No mutation detected | 79 | F | unknown | IPMN |
| 53 | No mutation detected | No mutation detected | 72 | F | unknown | IPMN |
| 54 | G12D                 | R201C              | 76 | F | unknown | IPMN |
| 55 | No mutation detected | R201H              | 61 | M | unknown | IPMN |
| 56 | G12V                 | R201C              | 86 | M | unknown | IPMN |
| 57 | G12R                 | R201C              | 68 | M | unknown | IPMN |
| 58 | G12D                 | No mutation detected | 66 | M | unknown | IPMN |
| 59 | G12V                 | R201C              | 81 | M | unknown | IPMN |
| 60 | G12D & G12V          | No mutation detected | 68 | M | unknown | IPMN |
| 61 | G12V                 | No mutation detected | 80 | M | unknown | IPMN |
| 62 | G12V                 | R201H              | 74 | F | unknown | IPMN |
| 63 | G12V                 | R201C              | 65 | F | unknown | IPMN |
| 64 | G12V                 | No mutation detected | 72 | F | unknown | IPMN |
| 65 | G12D & G12R          | R201C              | 65 | F | unknown | IPMN |

FIG. 6 CONTINUE

FROM FIG. 6 CONTINUE

| | | | | |
|---|---|---|---|---|
| high | 0.8 | mixed | not determined | body | Cyst fluid |
| low | 5.6 | branch | not determined | head | Cyst fluid |
| intermediate | 4.5 | mixed | not determined | neck | Cyst fluid |
| low | 2.0 | branch | not determined | tail | Cyst fluid |
| low | 2.9 | branch | not determined | tail | Cyst fluid |
| low | 3.2 | branch | not determined | tail | Cyst fluid |
| high | 1.5 | main | not determined | body | Cyst fluid |
| intermediate | 3.0 | branch | not determined | body | Cyst fluid |
| low | 3.4 | branch | not determined | body | Cyst fluid |
| intermediate | 4.2 | mixed | not determined | body | Cyst fluid |
| high | 6.7 | main | not determined | body/tail | Cyst fluid |
| high | 8.5 | not determined | not determined | body/tail | Cyst fluid |
| intermediate | 1.5 | branch | not determined | head | Cyst fluid |
| intermediate | 1.5 | branch | not determined | head | Cyst fluid |
| intermediate | 2.0 | branch | not determined | head | Cyst fluid |
| high | 2.0 | main | not determined | head | Cyst fluid |
| high | 2.8 | mixed | not determined | head | Cyst fluid |
| high | 2.8 | main | not determined | head | Cyst fluid |
| high | 3.0 | branch | not determined | head | Cyst fluid |
| intermediate | 3.0 | mixed | not determined | head | Cyst fluid |
| high | 3.4 | branch | not determined | head | Cyst fluid |
| low | 3.4 | branch | not determined | head | Cyst fluid |
| intermediate | 3.5 | branch | not determined | head | Cyst fluid |

FROM FIG. 6 CONTINUE

| | FROM FIG. 6 CONTINUE | | | | TO FIG. 6 CONTINUE |
|---|---|---|---|---|---|
| 66 | G12V | No mutation detected | 76 | F | unknown | IPMN |
| 67 | G12V | R201C & R201H | 77 | F | unknown | IPMN |
| 68 | No mutation detected | R201C | 87 | F | unknown | IPMN |
| 69 | No mutation detected | R201C | 70 | M | unknown | IPMN |
| 70 | G12V | R201C | 52 | F | unknown | IPMN |
| 71 | G12V | No mutation detected | 73 | F | unknown | IPMN |
| 72 | G12D | R201H | 74 | F | unknown | IPMN |
| 73 | G12V | R201C | 63 | M | unknown | IPMN |
| 74 | No mutation detected | R201C | 63 | M | unknown | IPMN |
| 75 | No mutation detected | R201C | 67 | F | unknown | IPMN |
| 76 | G12D | No mutation detected | 79 | M | unknown | IPMN |
| 77 | G12V | No mutation detected | 86 | F | unknown | IPMN |
| 78 | G12D & G12V | R201C & R201H | 74 | M | unknown | IPMN |
| 79 | G12V & G12R | R201H | 70 | M | unknown | IPMN |
| 80 | No mutation detected | R201C | 68 | M | unknown | IPMN |
| 81 | G12D | No mutation detected | 77 | F | unknown | IPMN |
| 82 | G12V | R201C | 67 | M | unknown | IPMN |
| 83 | G12D & G12V | No mutation detected | 80 | F | unknown | IPMN |
| 84 | G12D | No mutation detected | 68 | F | unknown | IPMN |
| 85 | G12D & G12V | No mutation detected | 68 | F | unknown | IPMN |
| 86 | G12D & G12V | R201C | 69 | M | unknown | IPMN |
| 87 | G12D & G12V & G12R | R201C & R201H | 69 | M | unknown | IPMN |
| 88 | No mutation detected | R201C | 72 | M | unknown | IPMN |

| | | | | |
|---|---|---|---|---|
| intermediate | 3.9 | branch | not determined | head | Cyst fluid |
| intermediate | 4.0 | branch | not determined | head | Cyst fluid |
| intermediate | 4.0 | mixed | not determined | head | Cyst fluid |
| high | 4.0 | mixed | not determined | head | Cyst fluid |
| high | 4.2 | mixed | not determined | head | Cyst fluid |
| intermediate | 4.5 | branch | not determined | head | Cyst fluid |
| intermediate | 5.0 | branch | not determined | head | Cyst fluid |
| high | 6.0 | main | not determined | head | Cyst fluid |
| high | 6.5 | mixed | not determined | head | Cyst fluid |
| high | 7.0 | main | not determined | head | Cyst fluid |
| low | 13.0 | main | not determined | head | Cyst fluid |
| intermediate | 1.7 | branch | not determined | tail | Cyst fluid |
| intermediate | 2.0 | mixed | not determined | tail | Cyst fluid |
| intermediate | 2.2 | branch | not determined | tail | Cyst fluid |
| high | 2.5 | main | not determined | tail | Cyst fluid |
| high | 2.6 | mixed | not determined | tail | Cyst fluid |
| intermediate | 2.7 | branch | not determined | tail | Cyst fluid |
| intermediate | 3.5 | mixed | not determined | tail | Cyst fluid |
| intermediate | 6.0 | branch | not determined | tail | Cyst fluid |
| intermediate | 6.0 | branch | not determined | tail | Cyst fluid |
| high | 23.0 | main | not determined | tail | Cyst fluid |
| high | 23.0 | main | not determined | tail | Cyst fluid |
| high | 1.4 | main | not determined | head | Cyst wall |

| | | | | | | |
|---|---|---|---|---|---|---|
| 89 | G12D | R201C | 74 | M | Yes | IPMN |
| 90 | G12V | No mutation detected | 54 | F | No | IPMN |
| 91 | No mutation detected | R201H | 81 | M | No | IPMN |
| 92 | G12V | R201H | 63 | F | No | IPMN |
| 93 | G12D | R201C | 73 | M | No | IPMN |
| 94 | G12V | No mutation detected | 60 | M | No | IPMN |
| 95 | G12D | No mutation detected | 76 | F | No | IPMN |
| 96 | G12D & G12V | R201C | 65 | M | No | IPMN |
| 97 | G12V | R201H | 67 | F | No | IPMN |
| 98 | No mutation detected | R201C | 54 | M | Yes | IPMN |
| 99 | G12D | No mutation detected | 72 | M | Yes | IPMN |
| 100 | G12R | R201H | 73 | M | Yes | IPMN |
| 101 | No mutation detected | No mutation detected | 79 | F | Yes | IPMN |
| 102 | G12V | No mutation detected | 67 | F | Yes | IPMN |
| 103 | G12D | No mutation detected | 60 | F | Yes | IPMN |
| 104 | G12V | R201C | 54 | F | Yes | IPMN |
| 105 | G12V | R201H | 57 | M | Yes | IPMN |
| 106 | No mutation detected | No mutation detected | 71 | F | unknown | IPMN |
| 107 | G12D | No mutation detected | 71 | M | unknown | IPMN |
| 108 | G12D | R201H | 66 | M | unknown | IPMN |
| 109 | No mutation detected | R201H | 65 | F | unknown | IPMN |
| 110 | G12V | R201C | 56 | M | unknown | IPMN |

| | | | | |
|---|---|---|---|---|
| intermediate | 3.0 | main | gastric | body/tail | Cyst fluid |
| low | 2.0 | branch | gastric | body/tail | Cyst fluid |
| high | 1.8 | main | intestinal | body/tail | Cyst fluid |
| intermediate | 1.9 | branch | not determined | body/tail | Cyst fluid |
| intermediate | 3.2 | branch | gastric | body/tail | Cyst fluid |
| high | 4.0 | branch | pancreatobiliary | head | Cyst fluid |
| high | 1 | branch | gastric | head | Cyst fluid |
| intermediate | 1.5 | branch | gastric | head | Cyst fluid |
| high | 4 | branch | gastric | body/tail | Cyst fluid |
| intermediate | 4.0 | branch | gastric | body/tail | Cyst fluid |
| low | 0.5 | branch | gastric | head | Cyst fluid |
| intermediate | 3.0 | branch | gastric | head | Cyst fluid |
| high | 4.0 | main | gastric | head | Cyst fluid |
| intermediate | 0.6 | branch | not determined | head | Cyst fluid |
| intermediate | 1 | branch | gastric | head | Cyst fluid |
| intermediate | 1.7 | branch | gastric | head | Cyst fluid |
| intermediate | 4.5 | branch | gastric | body/tail | Cyst fluid |
| low | 1.7 | branch | gastric | head | Cyst fluid |
| low | 6.0 | branch | not determined | head | Cyst fluid |
| intermediate | 0.6 | branch | intestinal | head | Cyst fluid |
| intermediate | 1.8 | mixed | gastric | head | Cyst fluid |
| intermediate | 2 | main | gastric | head | Cyst fluid |

FIG. 6 CONTINUE

| | FROM FIG. 6 CONTINUE | | | | TO FIG. 6 CONTINUE |
|---|---|---|---|---|---|
| 111 | G12D | No mutation detected | 63 | M | unknown | IPMN |
| 112 | G12R | R201C | 62 | M | unknown | IPMN |
| 113 | G12D | R201C | 71 | M | unknown | IPMN |
| 114 | G12R | No mutation detected | 60 | M | No | IPMN |
| 115 | G12D | R201H | 70 | M | No | IPMN |
| 116 | No mutation detected | R201C | 62 | F | No | IPMN |
| 117 | G12D | R201C | 75 | M | unknown | IPMN |
| 118 | G12D | No mutation detected | 73 | F | Yes | IPMN |
| 119 | G12R | No mutation detected | 71 | F | No | IPMN |
| 120 | G12V | R201H | 72 | M | No | IPMN |
| 121 | No mutation detected | R201H | 77 | M | No | IPMN |
| 122 | G12V | R201H | 35 | M | No | IPMN |
| 123 | G12V | R201H | 69 | M | No | IPMN |
| 124 | G12V | No mutation detected | 64 | F | Yes | IPMN |
| 125 | No mutation detected | R201C | 76 | F | Yes | IPMN |
| 126 | G12D | No mutation detected | 69 | F | unknown | IPMN |
| 127 | G12D | R201H | 79 | F | unknown | IPMN |
| 128 | G12D | No mutation detected | 74 | M | unknown | IPMN |
| 129 | G12D | No mutation detected | 56 | M | unknown | IPMN |
| 130 | G12D & G12V | R201C | 68 | F | Yes | IPMN |
| 131 | G12V | R201C | 73 | F | Yes | IPMN |
| 132 | G12V & G12R | R201H | 71 | M | No | IPMN |

FIG. 6
CONTINUE

FROM FIG. 6 CONTINUE

| | | | | | |
|---|---|---|---|---|---|
| intermediate | 3.1 | branch | gastric | head | Cyst fluid |
| intermediate | 3.5 | branch | not determined | head | Cyst fluid |
| low | 3.5 | branch | gastric | head | Cyst fluid |
| high | 13.0 | mixed | pancreatobiliary | entire pancreas | Cyst wall |
| high | 4.0 | main | pancreatobiliary | head | Cyst wall |
| high | 6.0 | main | gastric | head | Cyst wall |
| high | 5.0 | not determined | gastric | head | Cyst wall |
| high | 2.8 | branch | gastric | head | Cyst wall |
| low | 4.0 | branch | intestinal | body/tail | Cyst wall |
| high | 7.0 | main | intestinal | body/tail | Cyst wall |
| high | 7.0 | main | intestinal | entire pancreas | Cyst wall |
| high | 8.0 | main | intestinal | head | Cyst wall |
| high | 5.1 | mixed | gastric | body/tail | Cyst wall |
| low | 2.0 | branch | intestinal | body/tail | Cyst wall |
| high | 1.5 | main | gastric | body/tail | Cyst wall |
| intermediate | 3.4 | mixed | not determined | entire pancreas | Cyst wall |
| high | 14 | main | gastric | head | Cyst wall |
| intermediate | 8.0 | main | gastric | head | Cyst wall |
| intermediate | 4 | branch | gastric | body/tail | Cyst fluid |
| intermediate | 2.5 | branch | intestinal | entire pancreas | Cyst fluid |
| high | 6.0 | mixed | gastric | body/tail | Cyst wall |
| intermediate | 3.0 | mixed | | | |

Table S3. Characteristics of patients with cyst types other than IPMN, including GNAS and KRAS mutation status.

| Cyst # | KRAS | GNAS | Age at surgery | Sex | History of smoking | Post-operative diagnosis | Cyst Grade | Cyst diameter (cm) | Cyst location | Sample type |
|---|---|---|---|---|---|---|---|---|---|---|
| OT01 | No mutation detected | No mutation detected | 57 | F | unknown | SCA | NA | 2.5 | head | Cyst fluid |
| OT02 | No mutation detected | No mutation detected | 58 | F | No | SCA | NA | 1.5 | Neck | Cyst fluid |
| OT03 | No mutation detected | No mutation detected | 54 | M | unknown | SCA | NA | 2 | head | Cyst fluid |
| OT04 | No mutation detected | No mutation detected | 57 | M | Yes | SCA | NA | 2 | body/tail | Cyst fluid |
| OT05 | No mutation detected | No mutation detected | 69 | F | unknown | SCA | NA | 3 | tail | Cyst fluid |
| OT06 | No mutation detected | No mutation detected | 57 | F | Yes | SCA | NA | 3 | body/tail | Cyst fluid |
| OT07 | No mutation detected | No mutation detected | 59 | F | No | SCA | NA | 3 | head | Cyst fluid |
| OT08 | No mutation detected | No mutation detected | 64 | F | No | SCA | NA | 3 | head | Cyst fluid |
| OT09 | No mutation detected | No mutation detected | 60 | F | unknown | SCA | NA | 3.1 | head | Cyst fluid |
| OT10 | No mutation detected | No mutation detected | 56 | M | Yes | SCA | NA | 4 | body | Cyst fluid |
| OT11 | No mutation detected | No mutation detected | 47 | F | Yes | SCA | NA | 4 | head | Cyst fluid |
| OT12 | No mutation detected | No mutation detected | 49 | F | unknown | SCA | NA | 4 | head | Cyst fluid |
| OT13 | No mutation detected | No mutation detected | 52 | M | unknown | SCA | NA | 4.5 | tail | Cyst fluid |
| OT14 | No mutation detected | No mutation detected | 58 | F | unknown | SCA | NA | 4.8 | tail | Cyst fluid |
| OT15 | No mutation detected | No mutation detected | 46 | M | Yes | SCA | NA | 5 | head | Cyst fluid |
| OT16 | No mutation detected | No mutation detected | 81 | M | unknown | SCA | NA | 5 | head | Cyst fluid |
| OT17 | No mutation detected | No mutation detected | 77 | F | unknown | SCA | NA | 6 | body | Cyst fluid |
| OT18 | No mutation detected | No mutation detected | 61 | F | unknown | SCA | NA | 6 | tail | Cyst fluid |
| OT19 | No mutation detected | No mutation detected | 72 | M | Yes | SCA | NA | 7 | body/tail | Cyst fluid |
| OT20 | No mutation detected | No mutation detected | 61 | F | unknown | SCA | NA | 7.5 | body | Cyst fluid |
| OT21 | No mutation detected | No mutation detected | 77 | F | Yes | SCA | NA | 8 | body/tail | Cyst fluid |
| OT22 | No mutation detected | No mutation detected | 55 | F | unknown | SCA | NA | 10 | tail | Cyst fluid |
| OT23 | No mutation detected | No mutation detected | 61 | M | unknown | SCA | NA | 13 | tail | Cyst fluid |
| OT24 | No mutation detected | No mutation detected | 43 | M | No | SCA | NA | 1.5 | head | Cyst fluid |
| OT25 | No mutation detected | No mutation detected | 63 | F | unknown | SCA | NA | 1.8 | body/tail | Cyst fluid |
| OT26 | No mutation detected | No mutation detected | 62 | F | No | SCA | NA | 10.5 | body/tail | Cyst fluid |
| OT27 | No mutation detected | No mutation detected | 57 | F | No | SCA | NA | 2.5 | body/tail | Cyst fluid |
| OT28 | No mutation detected | No mutation detected | 86 | F | No | SCA | NA | 2.5 | body/tail | Cyst fluid |
| OT29 | No mutation detected | No mutation detected | 58 | M | Yes | SCA | NA | 2.5 | body/tail | Cyst fluid |
| OT30 | No mutation detected | No mutation detected | 68 | F | unknown | SCA | NA | 2.5 | head | Cyst fluid |
| OT31 | No mutation detected | No mutation detected | 72 | F | unknown | SCA | NA | 2.8 | body/tail | Cyst fluid |
| OT32 | No mutation detected | No mutation detected | 63 | F | Yes | SCA | NA | 3 | body/tail | Cyst fluid |
| OT33 | No mutation detected | No mutation detected | 47 | F | Yes | SCA | NA | 3 | head | Cyst fluid |
| OT34 | No mutation detected | No mutation detected | 64 | M | Yes | SCA | NA | 3.5 | head | Cyst fluid |
| OT35 | No mutation detected | No mutation detected | 52 | F | No | SCA | NA | 3.5 | body/tail | Cyst fluid |
| OT36 | No mutation detected | No mutation detected | 71 | F | No | SCA | NA | 3.7 | body/tail | Cyst fluid |
| OT37 | No mutation detected | No mutation detected | 77 | F | Yes | SCA | NA | 4 | body/tail | Cyst fluid |
| OT38 | No mutation detected | No mutation detected | 36 | F | unknown | SCA | NA | 4.1 | head | Cyst fluid |

FROM FIG. 7

| OT39 | No mutation detected | No mutation detected | 74 | F |
|------|----------------------|----------------------|----|---|
| OT40 | No mutation detected | No mutation detected | 66 | M |
| OT41 | No mutation detected | No mutation detected | 40 | F |
| OT42 | No mutation detected | No mutation detected | 56 | F |
| OT43 | No mutation detected | No mutation detected | 19 | F |
| OT44 | No mutation detected | No mutation detected | 69 | M |
| OT45 | No mutation detected | No mutation detected | 32 | F |
| OT46 | No mutation detected | No mutation detected | 51 | F |
| OT47 | G12V                 | No mutation detected | 65 | F |
| OT48 | G12V                 | No mutation detected | 46 | F |
| OT49 | G12V                 | No mutation detected | 43 | F |
| OT50 | No mutation detected | No mutation detected | 46 | F |
| OT51 | No mutation detected | No mutation detected | 65 | F |
| OT52 | No mutation detected | No mutation detected | 60 | F |
| OT53 | No mutation detected | No mutation detected | 59 | F |
| OT54 | No mutation detected | No mutation detected | 52 | F |
| OT55 | No mutation detected | No mutation detected | 24 | F |
| OT56 | No mutation detected | No mutation detected | 43 | F |
| OT57 | No mutation detected | No mutation detected | 59 | F |
| OT58 | G12V                 | No mutation detected | 42 | F |
| OT59 | No mutation detected | No mutation detected | 34 | F |
| OT60 | G12D                 | No mutation detected | 57 | F |
| OT61 | G12R                 | No mutation detected | 66 | F |
| OT62 | G12R                 | No mutation detected | 39 | F |
| OT63 | No mutation detected | No mutation detected | 36 | F |
| OT64 | No mutation detected | No mutation detected | 54 | F |
| OT65 | No mutation detected | No mutation detected | 42 | F |
| OT66 | G12D                 | No mutation detected | 45 | F |
| OT67 | No mutation detected | No mutation detected | 36 | M |
| OT68 | No mutation detected | No mutation detected | 72 | M |
| OT69 | No mutation detected | No mutation detected | 74 | M |
| OT70 | No mutation detected | No mutation detected | 55 | F |

FROM FIG. 7

| | | | | | |
|---|---|---|---|---|---|
| unknown | SCA | NA | 4.5 | head | Cyst fluid |
| No | SCA | NA | 5 | body/tail | Cyst fluid |
| unknown | SCA | NA | 5.4 | body/tail | Cyst fluid |
| No | SCA | NA | 5.9 | body/tail | Cyst fluid |
| unknown | SCA | NA | 6.6 | head | Cyst fluid |
| unknown | SCA | NA | 7.5 | head | Cyst fluid |
| Yes | MCN | Not determined | 2.3 | body | Cyst fluid |
| Yes | MCN | Not determined | 2.5 | body | Cyst fluid |
| No | MCN | Not determined | 2.5 | tail | Cyst fluid |
| No | MCN | low | 2.5 | tail | Cyst fluid |
| Yes | MCN | Not determined | 3.2 | body | Cyst fluid |
| No | MCN | Not determined | 3.5 | body | Cyst fluid |
| Yes | MCN | Not determined | 4 | tail | Cyst fluid |
| Yes | MCN | low | 4 | body/tail | Cyst fluid |
| No | MCN | Not determined | 4.5 | tail | Cyst fluid |
| No | MCN | Not determined | 5 | body/tail | Cyst fluid |
| unknown | MCN | low | 5 | body/tail | Cyst fluid |
| Yes | MCN | Not determined | 5.5 | body | Cyst fluid |
| Yes | MCN | low | 7 | body/tail | Cyst fluid |
| No | MCN | Not determined | 8.5 | body/tail | Cyst fluid |
| unknown | MCN | low | 16 | head | Cyst fluid |
| No | MCN | low | 17 | body | Cyst fluid |
| Yes | MCN | low | 1.5 | head | Cyst fluid |
| unknown | MCN | low | 2.5 | body/tail | Cyst fluid |
| unknown | MCN | low | 3.5 | head | Cyst fluid |
| unknown | MCN | low | 5.5 | body/tail | Cyst fluid |
| unknown | MCN | intermediate | 7.4 | head | Cyst fluid |
| unknown | IOPN | high | 3.1 | head | Cyst fluid |
| unknown | IOPN | high | 4.5 | head | Cyst fluid |
| No | IOPN | high | 6.0 | head | Cyst fluid |
| Yes | IOPN | high | 6.0 | body/tail | Cyst fluid |
| unknown | IOPN | high | 10.0 | tail | Cyst fluid |

FROM FIG. 7 CONTINUE

FIG. 7
CONTINUE

Fig. 8
Table S4. Quantification of mutations in selected IPMNs containing both *GNAS* and *KRAS* mutations.

| IPMN # | KRAS mutant allele(s) | Major KRAS mutant allele | Major KRAS allele freq | Major KRAS allele fraction/total mutant alleles* |
|---|---|---|---|---|
| 31 | G12D & G12V & G12R | G12D | 29% | 97% |
| 36 | G12D | G12D | 18% | Not applicable |
| 41 | G12D | G12D | 3.0% | NA |
| 42 | G12D | G12D | 17% | NA |
| 43 | G12D | G12D | 33% | NA |
| 48 | G12R | G12S | 1.6% | NA |
| 57 | G12R | G12S | 0.8% | NA |
| 65 | G12D & G12R | G12D | 27% | 88% |
| 67 | G12V | G12V | 8.0% | NA |
| 72 | G12D | G12D | 36% | NA |
| 78 | G12D & G12V | G12V | 0.9% | 65% |
| 79 | G12V & G12R | G12V | 11% | 60% |
| 86 | G12D & G12V | G12V | 18% | 50% |
| 87 | G12D & G12V & G12R | G12V | 8% | 46% |
| 100 | G12R | G12S | 1.4% | NA |
| 105 | G12V | G12V | 1.0% | NA |
| 130 | G12D & G12V | G12V | 4.0% | 56% |

* NA = Not applicable because there was only a single mutation identified in the IPMN.

Fig. 9
Table S5. Comparison of mutational status in DNA from IPMNs and pancreatic adenocarcinomas from the same patients.

| IPMN # | Lesion | *KRAS* mutation | *GNAS* mutation |
|---|---|---|---|
| 9 | IPMN | G12V & G12D | R201H & R201C |
| | Cancer | G12V | R201H |
| 11 | IPMN | No mutation detected | R201C |
| | Cancer | No mutation detected | R201C |
| 20 | IPMN | G12V | R201C |
| | Cancer | G12V | R201C |
| 33 | IPMN | G12V | R201H |
| | Cancer | G12R | No mutation detected |
| 122 | IPMN | G12V | R201H |
| | Cancer | G12V | R201H |
| 125 | IPMN | No mutation detected | R201C |
| | Cancer | No mutation detected | R201C |
| 127 | IPMN | G12D | R201H |
| | Cancer | G12D | R201H |
| 131 | IPMN | G12V | R201C |
| | Cancer | G12V | R201C |

Table S6. Oligonucleotide primer and probe sequences.

| Gene | Used for: | 5'-Modification |
|---|---|---|
| PCR Amplification Primers | | |
| GNAS | GNAS Forward Primer | None |
| GNAS | GNAS Reverse Primer | None |
| KRAS | PCR forward primer | None |
| KRAS | PCR Reverse Primer | None |
| Ligation probes | | |
| GNAS | WT-specific probe | 6-FAM |
| GNAS | Mutant-specific probe | HEX |
| GNAS | Common anchoring probe | Phosphate |
| GNAS | WT-specific probe | 6-FAM |
| GNAS | Mutant-specific probe | HEX |
| GNAS | Common anchoring probe | Phosphate |
| KRAS | WT-specific probe | 6-FAM |
| KRAS | Mutant-specific probe | HEX |
| KRAS | Common anchoring probe | Phosphate |
| KRAS | WT-specific probe | 6-FAM |
| KRAS | Mutant-specific probe | HEX |
| KRAS | Common anchoring probe | Phosphate |

| Mutation | Sequence (5'-3')* |
|---|---|
| GNAS 201 R201C, R201H | GGCTTTGGTGAGATCCATTG |
| GNAS 201 R201C, R201H | TCCACCTGGAACTTGGTCTC |
| KRAS G12D, G12R, G12V | GATCATATTCGTCCACAAATGATTC |
| KRAS G12D, G12R, G12V | TGACTGAATATAAACTTGTGGTAGTTG |
| R201H | *ATG GAG AAC TTG ACG TCC TG*  TTC GCT GCC G |
| R201H | TTCGCTGCCA |
| R201H | TGT CCT GAC TTC  *GG TGT CCA CTA GTC ATG CTT* |
| R201C | *ATG GAG AAC TTG ACG TCC AC*  CTT CGC TGC C |
| R201C | CTT *CGC T*G*C T |
| R201C | GTG TCC TGA CTT  *GG TGT CCA CTA GTC ATG CTT* |
| G12D | *ATG GAG AAC TTG ACG TCC TC* CTA CGC CAC |
| G12D | TGCCT*ACGC*C*AT |
| G12D | CAG CTC CAA CTA  *GG TGT CCA CTA GTC ATG CTT* |
| G12R | TCC CGC GAA ATT AAT ACG AG *CTA CGC CACC* |
| G12R | CTA  CGC CAC G |
| G12R | AGC TCC AAC TAC CAC *GG TGT CCA CTA GTC ATG CTT* |

| FROM FIG. 10 CONTINUE | | |
|---|---|---|
| KRAS | WT-specific probe | 6-FAM |
| KRAS | Mutant-specific probe | HEX |
| KRAS | Common anchoring probe | Phosphate |
| | | TO FIG. 10 CONTINUE |
| BEAMing probes | | |
| GNAS | Detecting beads containing either WT or mutant sequences | ROX |
| GNAS | WT-specific probe | Cy3 |
| GNAS | Mutant-specific probe | Cy5 |
| GNAS | Detecting beads containing either WT or mutant sequences | ROX |
| GNAS | WT-specific probe | Cy3 |
| GNAS | Mutant-specific probe | Cy5 |
| KRAS | Detecting beads containing either WT or mutant sequences | ROX |
| KRAS | WT-specific probe | Cy3 |
| KRAS | Mutant-specific probe | Cy5 |
| KRAS | Detecting beads containing either WT or mutant sequences | ROX |
| KRAS | WT-specific probe | Cy3 |
| KRAS | Mutant-specific probe | Cy5 |
| KRAS | Detecting beads containing either WT or mutant sequences | ROX |
| KRAS | WT-specific probe | Cy3 |
| KRAS | Mutant-specific probe | Cy5 |

* INDICATES LNA LINKAGES; BOLD FONT INDICATES ADDITIONAL NUCLEOTIDES
USED TO DISCRIMINATE WT FROM MUTANT SEQUENCES IN THE LIGATION ASSAYS.

| | |
|---|---|
| | FROM FIG. 10 CONTINUE |
| G12V | *ATG GAG AAC TTG ACG TCC T*C CTA CGC CAC |
| G12V | CCT ACG CCA A |
| G12V | CAG CTC CAA CTA *GG TGT CCA CTA GTC ATG CTT* |
| | |
| R201C | CTGAAACAAAATTGAGGT |
| R201C | AGGACACgGCAGCGA |
| R201C | AGGACACaGCAGCGA |
| | |
| R201H | CTGAAACAAAATTGAGGT |
| R201H | CAGGACACGGCAGCG |
| R201H | CAGGACATGGCAGCG |
| | |
| G12D | TGACGATACAGCTAATTCA |
| G12D | GGAGCTGGTGGCGTA |
| G12D | GGAGCTGATGGCGTA |
| | |
| G12V | TGACGATACAGCTAATTCA |
| G12V | GGAGCTGGTGGCGTA |
| G12V | GGAGCTGTTGGCGTA |
| | |
| G12R | TGACGATACAGCTAATTCA |
| G12R | TGGAGCTCGTGGCGT |
| G12R | TGGAGCTCGTGGCGT |

FROM FIG. 10 CONTINUE

FIG. 10 CONTINUE

SEQUENCE LISTING

```
<160> NUMBER OF SEQ ID NOS: 37

<210> SEQ ID NO 1
<211> LENGTH: 60
<212> TYPE: DNA
<213> ORGANISM: Artificial Sequence
<220> FEATURE:
<223> OTHER INFORMATION: Probe
<221> NAME/KEY: misc_feature
<222> LOCATION: (13)...(48)
<223> OTHER INFORMATION: 36 bases from a genomic region of interest
<221> NAME/KEY: misc_feature
<222> LOCATION: (1)...(60)
<223> OTHER INFORMATION: n = A,T,C or G

<400> SEQUENCE: 1
tcccgcgacg acnnnnnnnn nnnnnnnnnn nnnnnnnnnn nnnnnnnngc tggagtcgcg      60

<210> SEQ ID NO 2
<211> LENGTH: 15
<212> TYPE: DNA
<213> ORGANISM: Artificial Sequence
<220> FEATURE:
<223> OTHER INFORMATION: Probe

<400> SEQUENCE: 2
tgatcccgcg acgac                                                       15

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
gaccgcgact ccagc                                                       15
```

-continued

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
ggctttggtg agatccattg                                                 20

<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
tccacctgga acttggtctc                                                 20

<210> SEQ ID NO 6
<211> LENGTH: 26
<212> TYPE: DNA
<213> ORGANISM: Artificial Sequence
<220> FEATURE:
<223> OTHER INFORMATION: Probe

<400> SEQUENCE: 6
gatcatattc gtccacaaaa tgattc                                          26

<210> SEQ ID NO 7
<211> LENGTH: 27
<212> TYPE: DNA
<213> ORGANISM: Artificial Sequence
<220> FEATURE:
<223> OTHER INFORMATION: Probe

<400> SEQUENCE: 7
tgactgaata taaacttgtg gtagttg                                         27

<210> SEQ ID NO 8
<211> LENGTH: 30
<212> TYPE: DNA
<213> ORGANISM: Artificial Sequence
<220> FEATURE:
<223> OTHER INFORMATION: Probe

<400> SEQUENCE: 8
atggagaact tgacgtcctg ttcgctgccg                                      30

<210> SEQ ID NO 9
<211> LENGTH: 10
<212> TYPE: DNA
<213> ORGANISM: Artificial Sequence
<220> FEATURE:
<223> OTHER INFORMATION: Probe

<400> SEQUENCE: 9
ttcgctgcca                                                            10

<210> SEQ ID NO 10
<211> LENGTH: 32
<212> TYPE: DNA
<213> ORGANISM: Artificial Sequence
<220> FEATURE:

```
<223> OTHER INFORMATION: Probe

<400> SEQUENCE: 10
tgtcctgact tcggtgtcca ctagtcatgc tt                                32

<210> SEQ ID NO 11
<211> LENGTH: 30
<212> TYPE: DNA
<213> ORGANISM: Artificial Sequence
<220> FEATURE:
<223> OTHER INFORMATION: Probe

<400> SEQUENCE: 11
atggagaact tgacgtccac cttcgctgcc                                   30

<210> SEQ ID NO 12
<211> LENGTH: 10
<212> TYPE: DNA
<213> ORGANISM: Artificial Sequence
<220> FEATURE:
<223> OTHER INFORMATION: Probe

<400> SEQUENCE: 12
cttcgctgct                                                         10

<210> SEQ ID NO 13
<211> LENGTH: 32
<212> TYPE: DNA
<213> ORGANISM: Artificial Sequence
<220> FEATURE:
<223> OTHER INFORMATION: Probe

<400> SEQUENCE: 13
gtgtcctgac ttggtgtcca ctagtcatgc tt                                32

<210> SEQ ID NO 14
<211> LENGTH: 29
<212> TYPE: DNA
<213> ORGANISM: Artificial Sequence
<220> FEATURE:
<223> OTHER INFORMATION: Probe

<400> SEQUENCE: 14
atggagaact tgacgtcctc ctacgccac                                    29

<210> SEQ ID NO 15
<211> LENGTH: 12
<212> TYPE: DNA
<213> ORGANISM: Artificial Sequence
<220> FEATURE:
<223> OTHER INFORMATION: Probe

<400> SEQUENCE: 15
tgcctacgcc at                                                      12

<210> SEQ ID NO 16
<211> LENGTH: 32
<212> TYPE: DNA
<213> ORGANISM: Artificial Sequence
<220> FEATURE:
<223> OTHER INFORMATION: Probe

<400> SEQUENCE: 16
cagctccaac taggtgtcca ctagtcatgc tt                                32
```

```
<210> SEQ ID NO 17
<211> LENGTH: 30
<212> TYPE: DNA
<213> ORGANISM: Artificial Sequence
<220> FEATURE:
<223> OTHER INFORMATION: Probe

<400> SEQUENCE: 17
tcccgcgaaa ttaatacgag ctacgccacc                                              30

<210> SEQ ID NO 18
<211> LENGTH: 10
<212> TYPE: DNA
<213> ORGANISM: Artificial Sequence
<220> FEATURE:
<223> OTHER INFORMATION: Probe

<400> SEQUENCE: 18
ctacgccacg                                                                    10

<210> SEQ ID NO 19
<211> LENGTH: 35
<212> TYPE: DNA
<213> ORGANISM: Artificial Sequence
<220> FEATURE:
<223> OTHER INFORMATION: Probe

<400> SEQUENCE: 19
agctccaact accacggtgt ccactagtca tgctt                                        35

<210> SEQ ID NO 20
<211> LENGTH: 29
<212> TYPE: DNA
<213> ORGANISM: Artificial Sequence
<220> FEATURE:
<223> OTHER INFORMATION: Probe

<400> SEQUENCE: 20
atggagaact tgacgtcctc ctacgccac                                               29

<210> SEQ ID NO 21
<211> LENGTH: 10
<212> TYPE: DNA
<213> ORGANISM: Artificial Sequence
<220> FEATURE:
<223> OTHER INFORMATION: Probe

<400> SEQUENCE: 21
cctacgccaa                                                                    10

<210> SEQ ID NO 22
<211> LENGTH: 32
<212> TYPE: DNA
<213> ORGANISM: Artificial Sequence
<220> FEATURE:
<223> OTHER INFORMATION: Probe

<400> SEQUENCE: 22
cagctccaac taggtgtcca ctagtcatgc tt                                           32

<210> SEQ ID NO 23
<211> LENGTH: 18
<212> TYPE: DNA
<213> ORGANISM: Artificial Sequence
<220> FEATURE:
<223> OTHER INFORMATION: Probe
```

```
<400> SEQUENCE: 23
ctgaaacaaa attgaggt                                                 18

<210> SEQ ID NO 24
<211> LENGTH: 15
<212> TYPE: DNA
<213> ORGANISM: Artificial Sequence
<220> FEATURE:
<223> OTHER INFORMATION: Probe

<400> SEQUENCE: 24
aggacacggc agcga                                                    15

<210> SEQ ID NO 25
<211> LENGTH: 15
<212> TYPE: DNA
<213> ORGANISM: Artificial Sequence
<220> FEATURE:
<223> OTHER INFORMATION: Probe

<400> SEQUENCE: 25
aggacacagc agcga                                                    15

<210> SEQ ID NO 26
<211> LENGTH: 18
<212> TYPE: DNA
<213> ORGANISM: Artificial Sequence
<220> FEATURE:
<223> OTHER INFORMATION: Probe

<400> SEQUENCE: 26
ctgaaacaaa attgaggt                                                 18

<210> SEQ ID NO 27
<211> LENGTH: 15
<212> TYPE: DNA
<213> ORGANISM: Artificial Sequence
<220> FEATURE:
<223> OTHER INFORMATION: Probe

<400> SEQUENCE: 27
caggacacgg cagcg                                                    15

<210> SEQ ID NO 28
<211> LENGTH: 15
<212> TYPE: DNA
<213> ORGANISM: Artificial Sequence
<220> FEATURE:
<223> OTHER INFORMATION: Probe

<400> SEQUENCE: 28
caggacatgg cagcg                                                    15

<210> SEQ ID NO 29
<211> LENGTH: 19
<212> TYPE: DNA
<213> ORGANISM: Artificial Sequence
<220> FEATURE:
<223> OTHER INFORMATION: Probe

<400> SEQUENCE: 29
tgacgataca gctaattca                                                19

<210> SEQ ID NO 30
<211> LENGTH: 15
```

```
<212> TYPE: DNA
<213> ORGANISM: Artificial Sequence
<220> FEATURE:
<223> OTHER INFORMATION: Probe

<400> SEQUENCE: 30
ggagctggtg gcgta                                                    15

<210> SEQ ID NO 31
<211> LENGTH: 15
<212> TYPE: DNA
<213> ORGANISM: Artificial Sequence
<220> FEATURE:
<223> OTHER INFORMATION: Probe

<400> SEQUENCE: 31
ggagctgatg gcgta                                                    15

<210> SEQ ID NO 32
<211> LENGTH: 19
<212> TYPE: DNA
<213> ORGANISM: Artificial Sequence
<220> FEATURE:
<223> OTHER INFORMATION: Probe

<400> SEQUENCE: 32
tgacgataca gctaattca                                                19

<210> SEQ ID NO 33
<211> LENGTH: 15
<212> TYPE: DNA
<213> ORGANISM: Artificial Sequence
<220> FEATURE:
<223> OTHER INFORMATION: Probe

<400> SEQUENCE: 33
ggagctggtg gcgta                                                    15

<210> SEQ ID NO 34
<211> LENGTH: 15
<212> TYPE: DNA
<213> ORGANISM: Artificial Sequence
<220> FEATURE:
<223> OTHER INFORMATION: Probe

<400> SEQUENCE: 34
ggagctgttg gcgta                                                    15

<210> SEQ ID NO 35
<211> LENGTH: 19
<212> TYPE: DNA
<213> ORGANISM: Artificial Sequence
<220> FEATURE:
<223> OTHER INFORMATION: Probe

<400> SEQUENCE: 35
tgacgataca gctaattca                                                19

<210> SEQ ID NO 36
<211> LENGTH: 15
<212> TYPE: DNA
<213> ORGANISM: Artificial Sequence
<220> FEATURE:
<223> OTHER INFORMATION: Probe

<400> SEQUENCE: 36
```

```
tggagctggt ggcgt                                                    15

<210> SEQ ID NO 37
<211> LENGTH: 15
<212> TYPE: DNA
<213> ORGANISM: Artificial Sequence
<220> FEATURE:
<223> OTHER INFORMATION: Probe

<400> SEQUENCE: 37
tggagctcgt ggcgt                                                    15
```

MUTATIONS IN PANCREATIC NEOPLASMS

This invention was made with funds from the United States government. The United States retains certain rights to the invention according to the terms of CA 43460, CA 57345, and CA 62924.

TECHNICAL FIELD OF THE INVENTION

This invention is related to the area of cancer markers. In particular, it relates to markers that are helpful for diagnosis, prognosis, and theranostics.

BACKGROUND OF THE INVENTION

Pancreatic cysts occur in more than 20% of patients evaluated at autopsy and in 2.4% to 13% of patients studied by abdominal imaging (CT scan or MRI) for reasons unrelated to pancreatic pathology (1-4). In view of the ever-increasing use of abdominal imaging and continuing improvements in the resolution of these technologies, the diagnosis of these lesions, often as incidental findings, can be expected to rise. They pose a challenging management problem because some cysts represent bona fide precursor lesions to invasive pancreatic ductal adenocarcinomas (PDAs), while others have minimal neoplastic potential (5). Yet, distinguishing cystic neoplasms from one another on the basis of clinical, imaging, and standard laboratory criteria is often not possible. Because of the diagnostic dilemmas posed by these lesions, and the potentially lethal consequences of an incorrect clinical diagnosis, some patients with harmless cysts are over-treated by surgical resection of the cyst and part of the pancreas (6). These pancreatectomies are major surgical procedures associated with significant morbidity and even rare mortality, prompting most investigators to adopt a watchful waiting approach with frequent imaging, sometimes employing endoscopic ultrasound (EUS) surveillance (7). New diagnostic modalities that will improve the management of the numerous patients with pancreatic cysts are therefore urgently needed.

There are three main types of pancreatic cystic neoplasms (8). Serous cystic adenomas (SCAs) account for ~10% of surgically resected cystic lesions of the pancreas (8, 9). These cysts are thought to be totally benign with essentially no likelihood of becoming invasive (that is, of becoming PDA). Intraductal papillary mucinous neoplasms (IPMNs), representing ~20% of surgically resected cystic lesions of the pancreas (8, 9), occur in either the main pancreatic duct and/or branch ducts. Those in the main ducts are most aggressive, as ~45% are found to have progressed to invasive carcinoma at the time of surgical resection (10). Those in branch ducts are found to have progressed to invasive carcinoma in ~20% of patients (10). IPMNs can also be classified into three histologic subtypes—intestinal, pancreatobiliary, and gastric—based on the resemblance of their epithelial cells to those of the corresponding normal tissues. The natural history of IPMNs, regardless of their histology or location within the pancreas, is not known with certainty because the lesions are often excised when they reach a certain size (3 cm diameter) or become symptomatic. However, based on the age of patients with resected lesions, there appears to be a 5-year lag time from non-invasive IPMN (average age 63.2 years) to invasive IPMN (average age 68.1 years) (11). The third type of pancreatic cystic neoplasms, representing 5 to 10% of surgically resected pancreatic cysts, are called Mucinous Cystic Neoplasms (MCNs) These progress to invasive carcinomas less often than IPMNs: only ~10% of MCNs contain an invasive component when surgically excised (12). Moreover, MCNs are less diagnostically challenging because most lesions occur in the body or tail of the pancreas in relatively young women. The average age of women with MCNs is more than 20 years less than that of patients with either SCAs or IPMNs (12). The remainder of surgically resected cystic lesions of the pancreas are a heterogeneous group of retention cysts, congenital cysts, and other rarer lesions.

PDAs can be divided into two types: those that develop in the absence of cystic lesions and those that develop from a cystic lesion. The vast majority of PDAs that develop from cystic lesions do so from IPMNs, as SCAs do not give rise to PDAs and MCNs are less common than IPMNs. Interestingly, the prognoses of patients with PDAs developed from IPMNs are different from those in patients with PDAs that develops in the apparent absence of IPMNs (11, 13). The survival of patients with surgically resected PDAs associated with IPMNs is as high as 45% at 5 years (11, 13). In contrast, survival is very rare in other PDA patients (14). While some of the difference in survival is due to differences in stage at diagnosis, investigators have suggested that "carcinoma arising in IPMNs is a different disease" from the more common type of PDA that develops without any associated cystic precursor (15).

There is a continuing need in the art to develop tools for detecting and distinguishing different forms of cancer so that appropriate treatments may be administered and inappropriate treatments unlikely to be successful may be withheld.

SUMMARY OF THE INVENTION

According to one aspect of the invention a method distinguishes between pancreatic serous cystic adenomas (SCA) and pancreatic intraductal papillary mucinous neoplasms (IPMN). A sample from pancreatic cyst fluid or pancreatic cyst wall tissue is tested for the presence of a mutation at codon 201 in GNAS (guanine nucleotide binding protein (G protein), alpha stimulating activity polypeptide 1). Detection of the mutation indicates IPMN and not SCA.

According to another aspect of the invention a method distinguishes between pancreatic mucinous cystic neoplasm (MCN) and pancreatic intraductal papillary mucinous neoplasms (IPMN). A sample from pancreatic cyst wall tissue is tested for the presence of a mutation at codon 201 in GNAS. Detection of the mutation indicates IPMN and not MCN.

According to still another aspect of the invention a method identifies pancreatic ductal adenocarcinomas (PDA) derived from pancreatic intraductal papillary mucinous neoplasms (IPMN). A sample from the pancreatic ductal adenocarcinoma tissue is tested for the presence of a mutation at codon 201 in GNAS. Detection of the mutation indicates derivation from IPMN and predicts longer term survival.

According to a further aspect of the invention a method detects a pancreatic intraductal papillary mucinous neoplasms (IPMN). A sample selected from the group consisting of blood, pancreatic juice, and stool is tested for the presence of a mutation at codon 201 in GNAS. Detection of the mutation is a diagnostic indicator of IPMN.

These and other embodiments which will be apparent to those of skill in the art upon reading the specification provide the art with methods for assessing, characterizing, and detecting pancreatic cancers, so that they can be better managed.

BRIEF DESCRIPTION OF THE DRAWINGS

(FIG. 2A) Schematic of the ligation assay. Oligonucleotide probes complementary to either the WT or mutant sequences were incubated with a PCR product containing the sequence of interest. The WT- and mutant-specific probes were labeled with the fluorescent dyes 6-FAM and HEX, respectively, and the WT-specific probe was 11 bases longer than the mutant-specific probe. After ligation to a common anchoring primer, the ligation products were separated on a denaturing polyacrylamide slab gel. Further details of the assay are provided in the Materials and Methods. (FIG. 2B) Examples of the results obtained with the ligation assay in the indicated patients. Templates were derived from DNA of normal duodenum or IPMN tissue. Each lane represents the results of ligation of one of four independent PCR products, each containing 200 template molecules. The probe in the left panel was specific to the GNAS R201H mutation and the probe on the right panel was specific for the GNAS R201C mutation.

(FIG. 4A) H&E-stained section of a formalin-fixed, paraffin embedded sample (shows two apparently independent IPMNs with distinct morphologies located close to one another. The IPMN of gastric epithelial subtype (black arrow) harbored a GNAS R201C and a KRAS G12'V while the IPMN showing the intestinal subtype (red arrow) contained a GNAS R201C mutation but no KRAS mutation. (FIG. 4B) H&E stained section of a different, typical IPMN (FIG. 4C) Same IPMN as in FIG. 4B after microdissection of the cyst wall.

FIG. 5. (Table S1.) Genes analyzed by massively parallel sequencing in IPMN cyst fluids.

FIG. 6. (Table S2.) Characteristics of patients with IPMNs analyzed in this study, including GNAS and KRAS mutation status.

FIG. 7. (Table S3.) Characteristics of patients with cyst types other than IPMN, including GNAS and KRAS mutation status.

FIG. 8. (Table S4.) Quantification of mutations in selected IPMNs containing both GNAS and KRAS mutations.

FIG. 9. (Table S5.) Comparison of mutational status in DNA from IPMNs and pancreatic adenocarcinomas from the same patients.

FIG. 10. (Table S6.) Oligonucleotide primer and probe sequences (SEQ ID NO: 4-38).

DETAILED DESCRIPTION OF THE INVENTION

Figure 1:
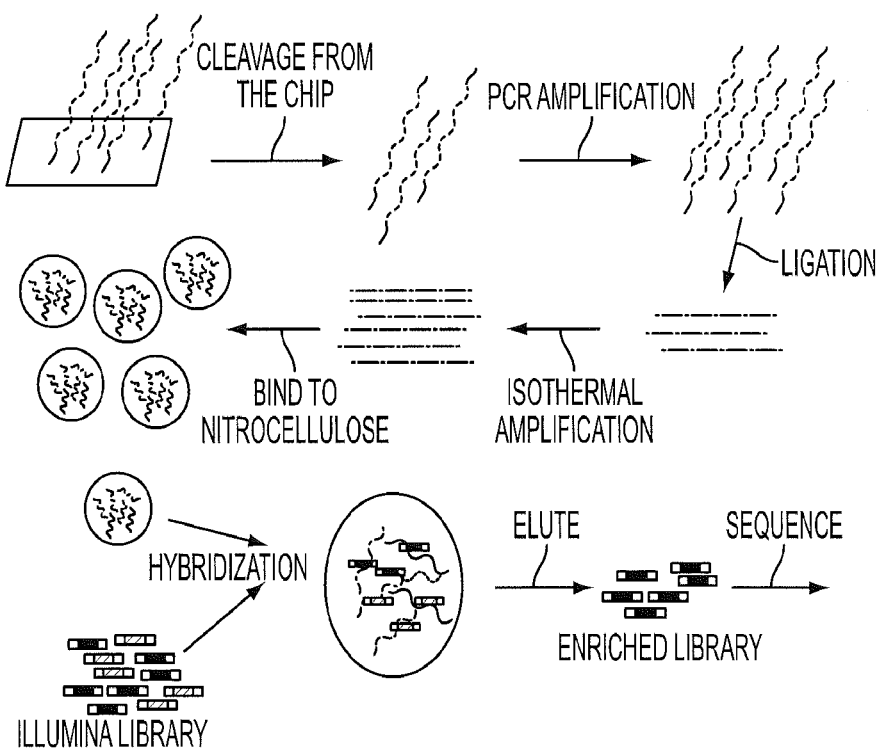
FIG. 1 provides a schematic of a capture strategy. Overlapping oligonucleotides flanked by universal sequences complimentary to the 169 genes listed in FIG. 5 (Table S1) were synthesized on an array. The oligonucleotides were cleaved off the array, amplified by PCR with universal primers, ligated into concatamers and amplified in an isothermal reaction. They were then bound to nitrocellulose filters and used as bait for capturing the desired fragments. An Illumina library was constructed from the sample DNA. The library was denatured and hybridized to the probes immobilized on nitrocellulose. The captured fragments were eluted, PCR amplified and sequenced on an Illumina GAIIX instrument.

What genetic features distinguish the Pancreatic Ductal Adenocarcinomas (PDAs) that develop from Intraductal Papillary Mucinous Neoplasms (IPMNs) from those that develop in their absence? As described below, the inventors have discovered that many PDAs developing in IPMNs contain GNAS (guanine nucleotide binding protein (G protein), alpha stimulating activity polypeptide 1) mutations while other PDAs do not. Moreover, these GNAS mutations generally occur early in IPMN development and can be used to distinguish IPMNs from other types of pancreatic cysts. Accordingly, GNAS mutations such as those in cyst fluids, for example, provide a highly specific biomarker that has the capacity to improve the diagnosis and management of patients with cystic lesions of the pancreas.

Test samples can be from any appropriate source in the patient's body that will have nucleic acids from a pancreatic lesion that can be collected and tested. In some cases the nucleic acids will be amplified prior to testing. Suitable test samples may be obtained from pancreatic cyst fluid, pancreatic cyst wall tissue, pancreatic ductal adenocarcinoma tissue, blood, stool, and pancreatic juice. The samples may be collected using any means conventional in the art, including from surgical samples, from biopsy samples, from endoscopic ultrasound (EUS), phlebotomy, etc. Obtaining the samples may be performed by the same person or a different person that conducts the subsequent analysis. Samples may be stored and/or transferred after collection and before analysis. Samples may be fractionated, treated, purified, enriched, prior to assay.

Any means of testing for a mutation in codon 201 of GNAS or codon 12 of KRAS may be used. Mutations may be detected by sequencing, by hybridization assay, by ligation assay, etc. Because the locations of the relevant mutations are defined, specific assays which focus on the identified locations may be used. Identifying a mutation as somatic can be accomplished by comparing a test sample to a non-neoplastic sample, either from the same patient or from a healthy individual. The wild type codon 201 encodes an arginine. Mutants may be any other codon, in particular one coding for histidine or for cysteine. A wild type KRAS codon 12 encodes a glycine, but it may be mutated to, for example, encode for aspartic acid, valine, or arginine. The defined locations of the mutations permit focused assays limited to an exon, domain, or codon. Any assay that is performed on a test sample involves a transformation, for example, a chemical or physical change or act. Assays and determinations are not performed merely by a perceptual or cognitive process in the body of a person.

Probes and/or primers may contain the wild-type or a mutant sequence. These can be used in a variety of different assays, as will be convenient for the particular situation. Selection of assays may be based on cost, facilities, equipment, electricity availability, speed, reproducibility, compatibility with other assays, invasiveness of sample collection, sample preparation, etc.

Any of the assay results may be recorded or communicated, as a positive act or step. Communication of an assay result, diagnosis, identification, or prognosis, may be, for example, orally between two people, in writing, whether on paper or digital media, by audio recording, into a medical chart or record, to a second health professional, or to a patient. The results and/or conclusions and/or recommendations based on the results may be in a natural language or in a machine or other code. Typically such records are kept in a confidential manner to protect the private information of the patient.

Collections of probes, primers, control samples, and reagents can be assembled into a kit for use in the methods. The reagents can be packaged with instructions, or directions to an address or phone number from which to obtain instructions. An electronic storage medium may be included in the kit, whether for instructional purposes or for recordation of results, or as means for controlling assays and data collection.

Control samples can be obtained from the same patient from a tissue that is not apparently diseased. Alternatively, control samples can be obtained from a healthy individual or a population of apparently healthy individuals. Control samples may be from the same type of tissue or from a different type of tissue than the test sample.

Alternatively to using nucleic acid assays for a codon mutation, protein based assays can be performed. For example, antibodies can be used which are specific for particular alternative residues in the GNAS protein at residue 201. Antibodies for wild type and or various mutant residues can be used. They can, for example, be differentially labeled. They can be used, for example, in separate assays and be similarly labeled or detected. Assays can also be based on differential protein activities of mutant and wild-type forms. Additionally, analyte levels can be assayed. High adenyl cyclase activity and cAMP levels Intraductal papillary mucinous neoplasms are characteristic of cells with GNAS mutations in codon 201.

The data described below document the existence of a heretofore unappreciated molecular pathway leading to pancreatic neoplasia. There is no doubt that GNAS mutations plays a driving role in this IPMN-specific pathway: the mutations are remarkably common and they occur at a single codon (201), mutations of which are known to endow cells with extremely high adenyl cyclase activity and cAMP levels (37-39). Based on their rate of mutation and specificity (30), the probability that these mutations are passengers rather than drivers of IPMN development is negligible.

Figure 4:
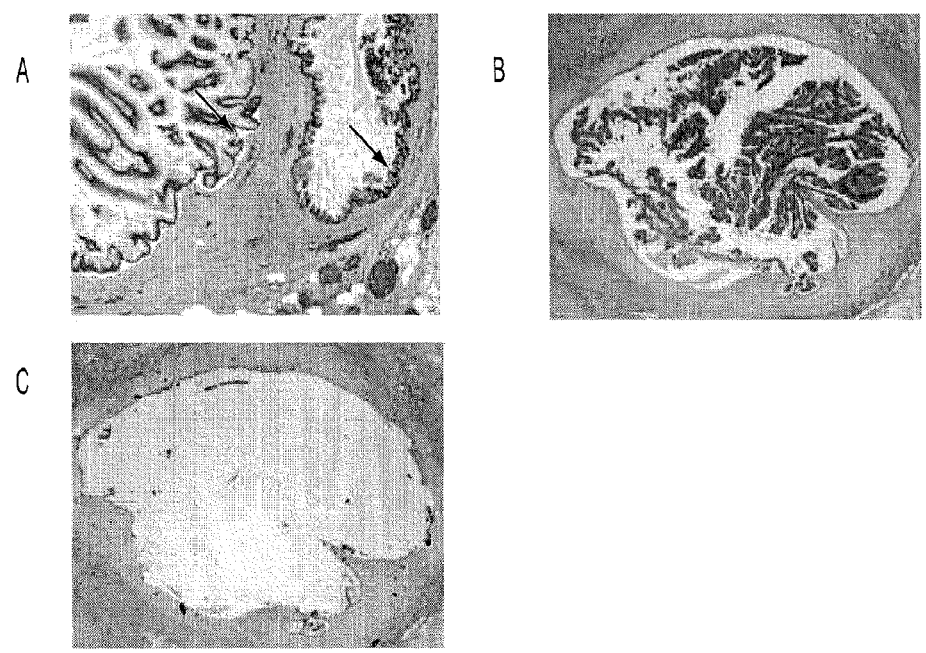
FIGS. 4A-4C show IPMN morphologies.

The data also demonstrated that >96% of IPMNs have either a GNAS or KRAS (v-Ki-ras2 Kirsten rat sarcoma viral oncogene homolog) mutation and more than half have both mutations. Which mutation—KRAS or GNAS—arises first? There were 20 cases in which GNAS mutations were identified in the absence of KRAS mutations and six additional cases in which GNAS mutations were at least 5 times more abundant than KRAS mutations in the same cyst fluid (FIG. 8 (Table S4)). The converse situation—KRAS mutations in the absence of GNAS mutations—was also observed in many cases (FIG. 6 (Table S2)). These data, in combination with the demonstration that more than one KRAS or more than one GNAS mutation could be identified in the same cyst (FIG. 8 (Table S4)), suggests two models for IPMN development. First, it is possible that IPMN locules represent independent entities whose evolution is unrelated to other locules within the same IPMN. This model is inconsistent with our data because two adjacent locules within a single grossly distinct IPMN were more likely to contain the same KRAS or GNAS mutation than the lining epithelium from two topographically different cysts, as noted in the Results section. Second, it is possible that all IPMNs are initiated by a single founding mutation in either GNAS or in KRAS. Subsequent mutations of cells within the cystic lesion would lead to independent clonal expansions, perhaps represented by different locules. Such polyclonality has been observed in colorectal adenomas, which are initiated by mutations in APC pathway genes but sometimes progress through heterogeneous KRAS mutations to a transient polyclonal stage (40). This stage is eventually replaced by subsequent clonal expansion of a cell with one of these KRAS mutations (40). A related possibility is that IPMNs are initiated by a genetic or epigenetic alteration in a gene other than KRAS or GNAS, and that we have observed subsequent clonal expansions of these initiated cells. Finally, it is possible that most IPMNs are indeed initiated by a mutation (in GNAS, KRAS, or another gene), but that occasionally two such IPMNs, initiated by completely different cells, develop adjacent to one another. This appeared to be the situation for the case shown in FIG. 4A, for example. Though these models are difficult to distinguish from one another, it is possible that lineage tracking can be accomplished by complete sequencing of IPMN locule genomes in the future (41).

Apart from its implications for understanding IPMN development, our data have potentially important practical ramifications. The appropriate management of a patient with a pancreatic cyst depends on the type of cyst (42). In particular, it is generally agreed that there is no need to remove asymptomatic SCAs because these lesions have a vanishingly small malignant potential (43). However, the distinction between SCA and mucinous cystic lesions (IPMN and MCN) of the pancreas is often not easy, even after extensive imaging and follow-up (6). One example of these difficulties is provided by the nature of the lesions in our study: the great majority of the 44 SCAs we examined were removed because they were preoperatively believed to be cysts with malignant potential. Hence, many of these 44 surgical procedures were likely unnecessary.

These diagnostic difficulties have long been appreciated and have spurred attempts to develop biomarkers as adjuncts to clinical data, imaging, and cytology (44). Indeed, new protein and glycoprotein markers are showing promising results (45, 46). One conceptual disadvantage of these protein biomarkers is that they are simply associated with cyst development and do not play a pathogenic role. Alterations of oncogenes such as KRAS are attractive alternatives because they are intimately involved in pathogenesis (47-50). In the largest previous study to date on such alterations, 45% of the fluids from mucinous cysts were shown to contain KRAS mutations (25). Our data demonstrates that KRAS mutations are actually present in a larger fraction of IPMNs, probably a result of the more sensitive methods used in our study combined with optimization of procedures used to purify cyst fluid DNA (see Materials and Methods). Third, and most important, the combination of GNAS and KRAS mutation detection provides high sensitivity and specificity for distinguishing between SCAs and IPMNs. The vast majority of IPMNs had a GNAS and/or a KRAS (95% CI 91% to 99%) while no SCAs had either mutation. These data indicate a sensitivity of 0.96 (95% CI 0.91 to 0.99) and a specificity of 1.0 (97.5% one-sided CI 0.92 to 1) for distinguishing between these two lesions. In addition, although not as sensitive, the presence of a GNAS mutation in cyst fluid can also distinguish IPMNs from MCNs (FIG. 7 (Table S3)). The assay involves just two amplicons (GNAS and KRAS) and can be performed with as little as 250 ul of cyst fluid.

Several caveats to the potential utility of such tests should be noted. First, the analysis of cyst fluid obtained through EUS, though safe, is an invasive procedure. Complications include bleeding, infection, and pancreatitis, are reversible, and are generally observed in <1% of patients (reviewed in (51)). Second, neither KRAS nor GNAS mutations can distinguish high grade or invasive from low grade IPMNs. The supplementation of KRAS and GNAS mutational analyses with other markers indicative of grade would clearly be useful (11). Third, we cannot yet reliably distinguish IPMNs from MCNs through the analysis of cyst fluid. Although MCNs do not contain GNAS mutations, a third of them contain KRAS mutations (FIG. 7 (Table S3)) MCN-specific mutations may be identified in the future through a strategy similar to the one we used to identify mutations in IPMNs.

Astute clinicians and pathologists have long suspected that adenocarcinomas of the pancreas arising in IPMNs are a "different disease" than those arising locally distant or in the absence of an IPMN (15, 52). We here provide evidence in support of this hypothesis and identify a key molecular component that underlies this difference.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods
Patients and Specimens

The present study was approved by the Institutional Review Boards of Johns Hopkins Medical Institutions, Memorial Sloan Kettering Cancer Center and the University of Indiana. We included individuals in whom pancreatic cyst fluid samples from pancreatectomy specimens and/or fresh frozen tumor tissues were available for molecular analysis. Relevant demographic, clinicopathologic data were obtained from prospectively maintained clinical databases and correlated with mutational status.

Pancreatic cyst fluids were harvested in the Surgical Pathology suite from surgically resected pancreatectomy specimens with a sterile syringe. Aspirated fluids were stored at −80° C. within 30 min of resection. Fresh-frozen tissue specimens of surgically resected cystic neoplasms of the pancreas were obtained through a prospectively maintained Johns Hopkins Surgical Pathology Tumor Bank. These lesions as well as normal tissues were macrodissected using serial frozen sections to guide the trimming of OCT embedded tissue blocks to obtain a minimum neoplastic cellularity of 80%. Formalin-fixed and paraffin-embedded archival tissues from surgically resected pancreata were sectioned at 6 μm, stained with hematoxylin and eosin, and dissected with a sterile needle on a SMZ1500 stereomicroscope (Nikon). An estimated 5,000-10,000 cells were microdissected from each lesion. Lesions were classified as IPMNs, MCNs, or SCAs using standard criteria (53). IPMNs were subtyped by internationally accepted criteria (54).

DNA Purification

DNA was purified from frozen cyst walls using an AllPrep kit (Qiagen) and from forrmalin-fixed, paraffin-embedded sections using the QIAamp DNA FFPE tissue kit (Qiagen) according to the manufacturer's instructions. DNA was purified from 250 μL of cyst fluid by adding 3 ml RLTM buffer (Qiagen) and then binding to an AllPrep DNA column (Qiagen) following the manufacturer's protocol. DNA was quantified in all cases with qPCR, employing primers and conditions as described (55).

Illumina Library Preparation

Cyst fluid DNA was first quantified through real-time PCR using primers specific for repeated sequences in DNA (LINE) as described (56). A minimum of 100 ng DNA from cyst fluid was used to make Illumina libraries according to manufacturer's protocol with the exception that the amount of adapters was decreased in proportional fashion when a lower amount of template DNA was used. The number of PCR cycles used to amplify the library after ligation of adapters was varied to ensure a yield of ~5 ug of the final library product for capture.

Target DNA Enrichment

The targeted region included all of the 3386 exons of 169 cancer related genes and was enriched with custom-made oligonucleotide probes. The design of each oligonucleotide was as follows: 5'-TCCCGCGACGAC—36 bases from the genomic region of interest—GCTGGAGTCGCG-3' (SEQ ID NO: 1). Probes were designed to capture both the plus and the minus strand of the DNA and had a 33-base overlap. The probes were custom-synthesized by Agilent Technology on a chip. The oligonucleotides were cleaved from the chip by treatment for five hours with 3 ml 35% ammonium hydroxide at room temperate. The solution was transferred to two 2-ml tubes, dried under vacuum, and re-dissolved in 400 ul RNase and DNase free water. Five ul of the solution were used for PCR amplification with primers complementary to the 12 base sequence common to all probes: 5-TGATCCCGCGACGA*C-3' (SEQ ID NO: 2), 5'-GACCGCGACTCCAG*C-3' (SEQ ID NO: 3), with * indicating a phosphorothioate bond. The PCR mix contained 27 ul $H_2O$, 5 ul template DNA, 2 ul forward primer (25 uM), 2 ul reverse primer (25 uM), 4 ul $MgCl_2$ (50 mM), 5 ul 10× Platinum Taq buffer (Life Technologies), 4 ul dNTPs (10 mM each) and 1 ul Platinum Taq (5 U/ul, Life Technologies). The cycling conditions were: one cycle of 98° C. for 30 s; 35 cycles of 98° C. for 30 s, 40° C. for 30 s, 60° C. for 15 s, 72° C. for 45 s; one cycle of 72° C. for 5 min. The PCR product was purified using a MinElute Purification Column (Qiagen) and end-repaired using End-IT DNA End-Repair Kit (Epicentre) as follows: 34 ul DNA, 5 ul 10× End-Repair Buffer, 5 ul dNTP Mix, 5 ul ATP, 1 ul End-Repair Enzyme Mix. The mix was incubated at room temperature for 45 minutes, and then purified using a MinElute Purification Column (Qiagen). The PCR products were ligated to form concatamers using the following protocol: 35 ul End-Repaired DNA product, 40 ul 2× T4 DNA ligase buffer, 5 ul T4 DNA ligase (3000 units; Enzymatics Inc.) The mix was incubated at room temperature for 4 hours, then purified using QiaQuick Purification Column (Qiagen), and quantified by absorption at 260 nm.

Replicates of 50 ng of concatenated PCR product were amplified in 25 ul solution using the REPLI-g midi whole genome amplification kit (Qiagen) according to the manufacturer's protocol. The RepliG-amplified DNA (20 ug) was then bound to a nitrocellulose membrane and used to capture DNA libraries as described (57). In general, 5 ug of library DNA were used per capture. After washing, the captured libraries were ethanol precipitated and redissolved in 20 ul TE buffer. The DNA was then amplified in a PCR mix containing 51 ul dH$_2$O, 20 ul 5× Phusion buffer, 5 ul DMSO, 2 ul 10 mM dNTPs, 50 pmol Illumina forward and reverse primers, and 1 ul Hotstart Phusion enzyme (New England Biolabs) using the following cycling program: 98° C. for 30 sec; 15 cycles of 98° C. for 25 sec., 65° C. for 30 sec, 72° C. for 30 sec; and 72° C. for 5 min. The amplified PCR product was purified using a NucleoSpin column (Macherey Nagel, inc.) according to the manufacturer's suggested protocol except that the NT buffer was not diluted and the DNA bound to the column was eluted in 35 ul elution buffer. The captured library was quantified with realtime PCR with the primers used for grafting to the Illumina sequencing chip.

Ligation Assay

PCR products containing codon 12 of KRAS and codon 201 of GNAS were amplified using the primers described in FIG. 10 (Table S6). Each 10-ul PCR contained 200 template molecules in 5 ul of 2× Phusion Flash PCR Master Mix (New England Biolabs) and final concentrations of 0.25 uM forward and 1.5 uM reverse primers. Note that the mutant-specific probes sometimes included locked nucleic acid residues (FIG. 10 (Table S6); Exiqon). The following cycling conditions were used: 98° C. for 2 min; 3 cycles of 98° C. for 10 sec., 69° C. for 15 sec, 72° C. for 15 sec; 3 cycles of 98° C. for 10 sec., 66° C. for 15 sec, 72° C. for 15 sec; 3 cycles of 98° C. for 10 sec., 63° C. for 15 sec, 72° C. for 15 sec; 41 cycles of 98° C. for 10 sec., 60° C. for 60 sec. Reactions were performed in at least quadruplicate and each was evaluated independently. Five ul of a solution containing 0.5 ul of Proteinase K, (18.8 mg/ml, Roche) and 4.5 ul of dH$_2$O was added to each well and incubated at 60° C. for 30 minutes to inactivate the Phusion polymerase and then for 10 min at 98° C. to inactivate the Proteinase K.

The ligation assay was based on techniques described previously, using thermotolerant DNA ligases (58-61). Each 10-ul reaction contained 2-ul of PCR product (unpurified), 1 ul of 10× Ampligase buffer (Epicentre), 0.5 ul of Ampligase (5 U/ul, Epicentre), anchoring primer (final concentration 2 uM), WT-specific primer (final concentration 0.1 uM), and mutant-specific primer (final concentration 0.025 uM). The sequences of these primers are listed in FIG. 10 (Table S6). The following cycling conditions were used: 95° C. for 3 min; 35 cycles of 95° C. for 10 sec., 37° C. for 30 sec, 45° C. for 60 sec. Five ul of each reaction was added to 5 ul of formamide and the ligation products separated on a 10% Urea-Tris-Borate-EDTA gel (Invitrogen) and imaged with an Amersham-GE Typhoon instrument (GE Healthcare).

BEAMing Assays

These were performed as described (62) using the PCR products generated for the ligation assay as templates and the oligonucleotides listed in FIG. 10 (Table S6) as hybridization probes.

Statistical Analysis

Fisher's exact tests were used to compare the differences between proportions and Wilcoxon Rank Sum tests were used to compare differences in mutational status by age. Confidence intervals for the prevalence of mutations were estimated using the binomial distribution. To compare the prevalence of mutations in grossly distinct IPMNs to adjacent locules within a single grossly distinct IPMN, we compared the probability of observing given KRAS or GNAS mutation in the 111 distinct IPMNs to conditional probability that given the first locule sequenced contained a specific KRAS or GNAS mutation all other locules contained the same KRAS or GNAS mutations. The probabilities of GNAS or KRAS mutations occurring by chance was calculated using a binomial distribution and the previously estimated mutation rates of tumors or normal cells (30). STATA version 11 was used for all statistical analysis (63).

Example 2

Massively Parallel Sequencing of 169 Genes in Cyst Fluid DNA

To initiate this study, we determined the sequences of 169 presumptive cancer genes in the cyst fluids of 19 IPMNs, each obtained from a different patient. Thirty-three of the 169 were oncogenes and the remainder were tumor suppressor genes. Though only a tiny subset of these 169 genes were known to be mutated in PDAs, all were known to be frequently mutated in at least one solid tumor type (FIG. 5 (Table S1)). We additionally sequenced these genes in normal pancreatic, splenic or intestinal tissues of the same patients to determine which of the alterations identified were somatic. We chose to use massively parallel sequencing rather than Sanger sequencing for this analysis because we did not know what fraction of DNA purified from the cyst fluid was derived from neoplastic cells. Massively parallel sequencing has the capacity to identify mutations present in 2% or more of the studied cells while Sanger sequencing often requires >25% neoplastic cells for this purpose. IPMNs are by definition connected with the pancreatic duct system and the cyst fluid containing cellular debris and shed DNA from the neoplastic cells can be expected to be admixed with that of the cells and secretions derived from normal ductal epithelial cells.

We devised a strategy to capture sequences of the 169 genes from cyst fluid DNA (FIG. 1). In brief, 244,000 oligonucleotides, each 60 bp in length and in aggregate covering the exonic sequences of all 169 genes, were synthesized in parallel using phosphoramadite chemistry on a single chip synthesized by Agilent Technologies. After removal from the chip, the oligonucleotide sequences were amplified by PCR and ligated together. Multiple displacement amplification was then used to further amplify the oligonucleotides, which were then bound to a filter. Finally, the filter was used to capture complementary DNA sequences from the cyst fluids and corresponding normal samples, and the captured DNA was subjected to massively parallel sequencing.

The target region corresponding to the coding exons of the 169 genes encompassed 584,871 bp. These bases were redundantly sequenced, with 902±411 (mean 1 SD) fold-coverage in the 38 samples sequenced (19 IPMN cyst fluids plus 19 matched DNA samples from normal tissues of the same patients). This coverage allowed us to confidently detect somatic mutations present in >5% of the template molecules.

There were only two genes mutated in more than one IPMN-KRAS, which was mutated in 14 of the 19 IPMNs, and GNAS, which was mutated in 6 IPMNs. The mutations in GNAS all occurred at codon 201, resulting in either a R201H or R201C substitution. GNAS is a well-known oncogene that is mutated in pituitary and other uncommon tumor types (16-19). However, such mutations have rarely been reported in common epithelial tumors (20-22). In pituitary tumors, mutations cluster at two positions—codons 201 and 227 (16, 19). This clustering provides extraordinary opportunities for diagnosis, similar to that of KRAS. For example, the clustering of KRAS mutations has facilitated the design of assays to detect mutations in tumors of colorectal cancer patients eligible for therapy with antibodies to EGFR (23). All twelve KRAS mutations identified through massively parallel sequencing of cyst fluids were at codon 12, resulting in a G12D, G12V, or G12R amino acid change. KRAS mutations at codon 12 have previously been identified in the vast majority of PDAs as well as in 40 to 60% of IPMNs (24-29). GNAS mutations have not previously been identified in pancreatic cysts or in PDAs.

Example 3

Frequency of KRAS and GNAS Mutations in Pancreatic Cyst Fluid DNA

We next determined the frequency of KRAS codon 12 and GNAS codon 201 mutations in a larger set of IPMNs. The clinical characteristics of all IPMNs analyzed in this study are listed in FIG. 6 (Table S2). To ensure that the analyses were performed robustly, we carried out preliminary experiments with cyst fluids from patients with known mutations based on the massively parallel sequencing experiments described above. We tested several methods for purifying DNA from often viscous cyst fluids and used the optimum method for subsequent experiments. Quantitative PCR was used to determine the number of amplifiable template molecules recovered with this procedure. In eight cases, we compared pelleted cells to supernatants derived from the same cyst fluid samples and found that the fraction of mutant templates in both compartments was similar. On the basis of these results, we purified DNA from 0.25 ml of whole cyst fluid (cells plus supernatant) and, as assessed by quantitative PCR, recovered an average of 670±790 ng of usable DNA.

Figure 2A:
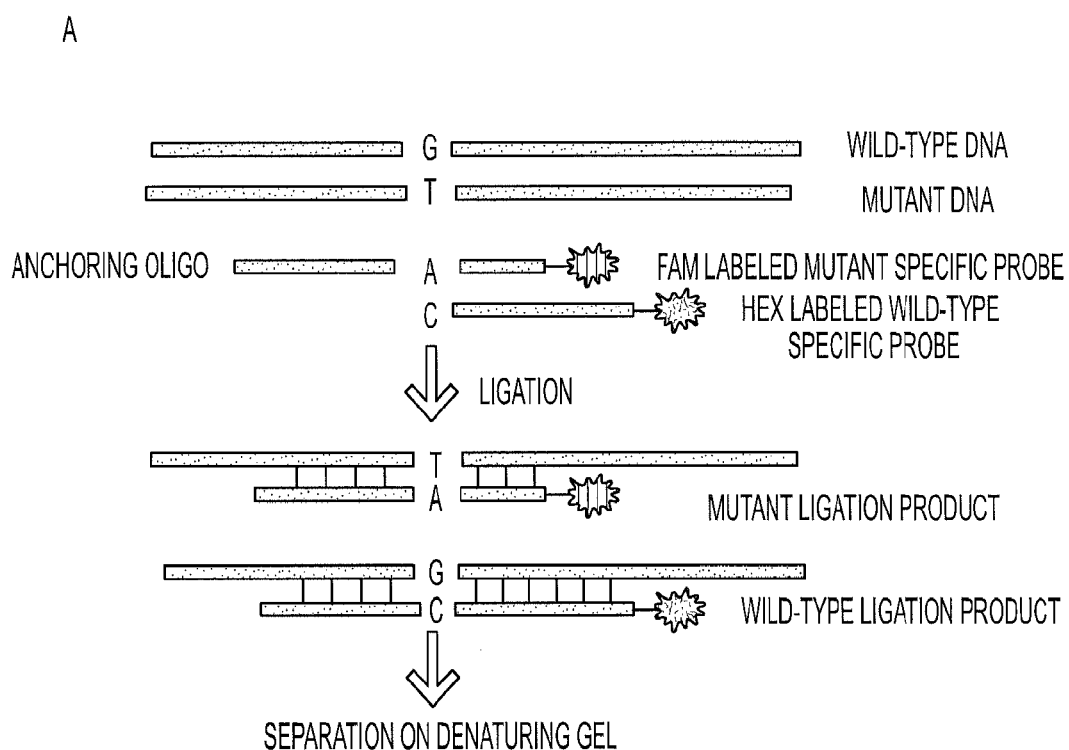
FIGS. 2A-2B show a ligation assays used to assess KRAS (v-Ki-ras2 Kirsten rat sarcoma viral oncogene homolog) and GNAS (guanine nucleotide binding protein (G protein), alpha stimulating activity polypeptide 1) mutations.
Figure 2B:
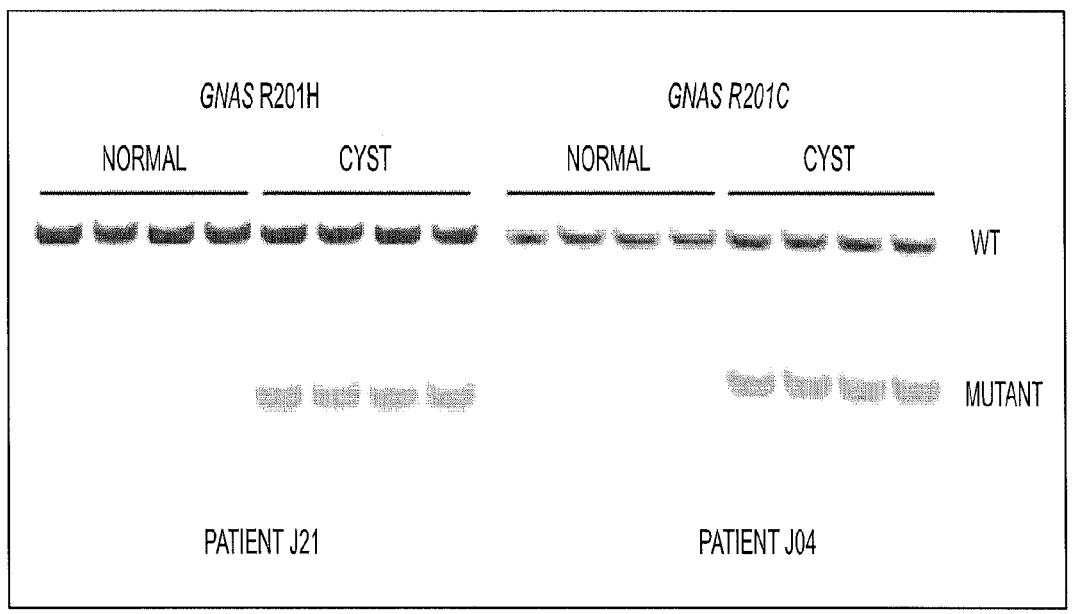

For each of 84 cyst fluid samples (an independent cohort of 65 patients plus the 19 patients whose fluids had been studied by massively parallel sequencing), we analyzed ~800 template molecules for five distinct mutations, three at KRAS codon 12 and two within GNAS codon 201 (see Materials and Methods). A PCR/ligation method that had the capacity to detect one mutant template molecule among 200 normal (wild-type, WT) templates was used for these analyses (FIG. 2A). We identified GNAS and KRAS mutations in 61% and 82% of the IPMN fluids, respectively (representative examples in FIG. 2B). In those samples without GNAS codon 201 mutations, we searched for GNAS codon 227 mutations, but did not find any. We also analyzed macro- and microdissected frozen or paraffin-embedded cyst walls from an independent collection of 48 surgically resected IPMNs, and similarly identified a high prevalence of GNAS (75%) and KRAS (79%) mutations. In aggregate, 66% of 132 IPMNs harbored a GNAS mutation, 81% harbored a KRAS mutation, slightly more than half (51%) harbored both GNAS and KRAS mutations, while at least one of the two genes was mutated in 96.2% (FIG. 6 (Table S2)). Given background mutation rates in tumors or normal tissues (30), the probability that either GNAS or KRAS mutations occurred by chance alone was less than $10^{-30}$. There were no significant correlations between the prevalence of KRAS or GNAS mutations and age, sex, or smoking history of the patients (P>0.05) (Table 1). Small (<3 cm) as well as larger cysts had similar fractions of both KRAS and GNAS mutations and the location of the IPMN (head, body, or tail) did not correlate with the presence of mutation in either gene (Table 1). GNAS and KRAS mutations were present in low-grade as well as in high-grade IPMNs. The prevalence of KRAS mutations was higher in lower grade lesions (P=0.03) whereas the prevalence of GNAS mutations was somewhat higher in more advanced lesions (P=0.11) (Table 1). GNAS, as well as KRAS mutations were present in each of the three major histologic types of IPMNs—intestinal, pancreatobiliary, and gastric. However, the prevalence of the mutations varied across the histological types (P<0.01 for both KRAS and GNAS). GNAS mutations were most prevalent in the intestinal subtype (100%), KRAS mutations had the highest frequency (100%) in the pancreatobiliary subtype and had the lowest frequency (42%) in the intestinal subtype (Table 1).

We then determined whether GNAS mutations were present in SCAs, a common but benign type of pancreatic cystic neoplasm. We examined a total of 44 surgically resected SCAs, each from a different patient (42 cyst fluids and 2 cyst walls). Many of these cysts were surgically resected because they clinically mimicked an IPMN. They would have likely not been surgically excised had they been known to be SCAs. The SCAs averaged 5.0±2.8 cm in maximum diameter (FIG. 7 (Table S3)) similar to the IPMNs (4.4±3.7 maximum diameter, FIG. 6 (Table S2)). There was little difference in the locations of the SCAs and IPMNs within the pancreas (FIGS. 6 and 7 (Tables S2 and S3)). However, no GNAS or KRAS mutations were identified in the SCAs, in marked contrast to the IPMNs (p<0.001, Fisher's Exact Test). GNAS mutations were also not identified in any of 21 MCNs (p=0.005 when compared to IPMNs, Fisher's Exact Test), although KRAS mutations were found in 33% of MCNs (FIG. 7 (Table S3)). GNAS mutations were also not identified in five examples of an uncommon type of cyst, called intraductal oncocytic papillary neoplasm (IOPN), with characteristic oncocytic features (FIG. 7 (Table S3)).

TABLE 1

Correlations between mutations and clinical and histopathologic parameters of IPMNs

|  |  | N, total | KRAS mutation | | | GNAS mutation | | |
| --- | --- | --- | --- | --- | --- | --- | --- | --- |
|  |  |  | N | % | P-value | N | % | P-value |
| Age in years | <65 years | 29 | 22 | 75.9 | 0.42 | 18 | 62.1 | 0.62 |
|  | ≥65 years | 103 | 85 | 82.5 |  | 69 | 67 |  |
| Gender | Male | 70 | 58 | 82.9 | 0.58 | 51 | 72.9 | 0.07 |
|  | Female | 62 | 49 | 79 |  | 36 | 58.1 |  |
| History of smoking | Yes | 25 | 21 | 84 | 0.77 | 17 | 68 | 0.85 |
|  | No | 37 | 30 | 81.1 |  | 26 | 70.3 |  |
| Grade | Low | 23 | 20 | 87 | 0.43 | 11 | 47.8 | 0.04 |
|  | Intermediate | 51 | 46 | 90.2 | (low vs. | 34 | 66.7 | (low vs. |
|  | High | 58 | 41 | 70.7 | others) | 42 | 72.4 | others) |
| Duct type | Main | 35 | 23 | 65.7 | 0.002 | 24 | 68.6 | 0.37 |
|  | Branch | 64 | 58 | 90.6 | (main vs. | 38 | 59.4 | (main vs. |
|  | Mixed | 28 | 21 | 75 | branch) | 20 | 71.4 | branch) |

TABLE 1-continued

Correlations between mutations and clinical and histopathologic parameters of IPMNs

|  |  | N, total | KRAS mutation | | | GNAS mutation | | |
|---|---|---|---|---|---|---|---|---|
|  |  |  | N | % | P-value | N | % | P-value |
| Subtype | Gastric | 52 | 45 | 86.5 | 0.02 | 34 | 65.4 | 0.002 |
|  | Pancreatobiliary | 7 | 7 | 100 | (panc. vs | 3 | 42.9 | (panc. vs |
|  | Intestinal | 13 | 6 | 46.2 | intestinal) | 13 | 100 | intestinal) |
| Diameter | <3 cm | 62 | 49 | 79 | 0.58 | 41 | 66.1 | 0.96 |
|  | ≥3 cm | 70 | 58 | 82.9 |  | 46 | 65.7 |  |
| Location | Proximal (head) | 77 | 64 | 83.1 | 0.44 (prox. vs | 53 | 68.8 | 0.38 (prox. vs |
|  | Distal (body, tail) | 49 | 38 | 77.6 | distal) | 30 | 61.2 | distal) |
|  | Proximal and distal | 6 | 5 | 83.3 |  | 4 | 66.7 |  |
| Associated cancer | Yes | 24 | 18 | 75 | 0.4 | 18 | 75 | 0.3 |
|  | No | 108 | 89 | 82.4 |  | 69 | 63.9 |  |

Example 4

IPMN Polyclonality

KRAS G12D, G12V, and G12R mutations were found in 43%, 39%, and 13% of IPMNs, respectively (FIG. 6 (Table S2)). A small fraction (11%) of the IPMNs contained two different KRAS mutations and 2% contained three different mutations. Likewise, GNAS R201C and GNASR201H mutations were present in 39% and 32% of the IPMNs, respectively, and 4% of the IPMNs had both mutations (FIG. 6 (Table S2)). More than one mutation in KRAS in IPMNs has been observed in prior studies of IPMNs (31-33) and the multiple KRAS and GNAS mutations are suggestive of a polyclonal origin of the tumor.

Figure 3:
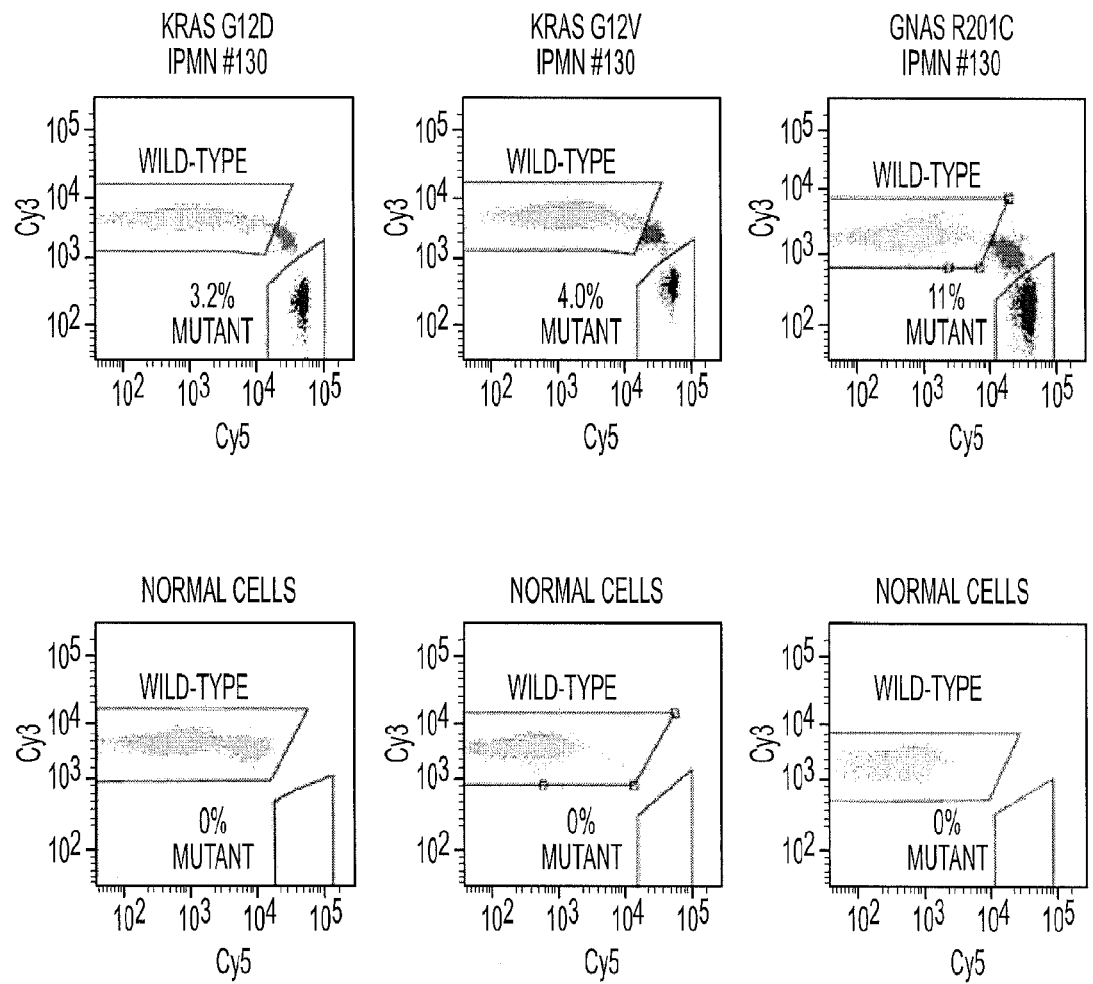
FIG. 3 shows BEAMing assays used to quantify mutant representation. PCR was used to amplify KRAS or GNAS sequences containing the region of interest (KRAS codon 12 and GNAS codon 201). The PCR-products were then used as templates for BEAMing, in which each template was converted to a bead containing thousands of identical copies of the templates (34). After hybridization to Cy3- or Cy5-labeled oligonucleotide probes specific for the indicated WT or mutant sequences, respectively, the beads were analyzed by flow cytometry. Scatter plots are shown for templates derived from the DNA of IPMN 130 or from normal spleen. Beads containing the WT or mutant sequences are widely separated in the scatter plots, and the fraction of mutant-containing beads are indicated. Beads whose fluorescence spectra lie between the WT and mutant-containing beads result from inclusion of both WT and mutant templates in the aqueous nanocompartments of the emulsion PCR.

We investigated clonality in more detail by precisely quantifying the levels of mutations in the subset of cyst fluids containing more than one mutation of the same gene. To accomplish this, we used a technique called BEAMing (34). Through this method, individual template molecules are converted into individual magnetic beads attached to thousands of molecules with the identical sequence. The beads are then hybridized with mutation-specific probes and analyzed by flow cytometry (FIG. 3). The analysis of 17 IPMN cyst fluids, each with mutations in both KRAS and GNAS, showed that the fraction of mutant alleles varied widely, ranging from 0.8% to 45% of the templates analyzed. There was an average of 12.8%±12.2% mutant alleles of KRAS and an average of 24.4±13.1% mutant alleles of GNAS in the 17 IPMN cyst fluids examined (FIG. 8 (Table S4)). In two of the seven IPMNs with more than one KRAS mutation, there was a predominant mutant that out-numbered the second KRAS mutant by >5:1 (FIG. 8 (Table S4)). Similarly, two of the four cases harboring two different GNAS mutations had a predominant mutant (FIG. 8 (Table S4)). In the other cases, the different mutations in KRAS (or GNAS) were distributed more evenly (FIG. 8 (Table S4)). These data support the idea that cells within a subset of IPMNs had undergone independent clonal expansions, giving rise to apparent polyclonality (35).

IPMNs are often multilocular or multifocal in nature, looking much like a bunch of grapes (FIG. 4A) (36). To determine the relationship between cyst locules (individual grapes) and cyst fluid, we microdissected the walls from individual locules of each of ten IPMNs from whom cyst fluid was available (example in FIGS. 4B and C). The individual locule walls generally appeared to be monoclonal, as more than one KRAS mutation was only found in one (4.5%) of the 22 locules examined. No locule wall contained more than one GNAS mutation and two adjacent locules within a single grossly distinct IPMN were more likely to contain the same KRAS or GNAS mutation than the lining epithelium from two topographically different IPMNs (p<0.05, Fisher's Exact Test for KRAS G12D, KRAS G12R and GNAS R201H mutations; P<0.10 for KRAS G12V and GNAS R201H mutations). All of the ten KRAS and six GNAS mutations identified in the cyst fluid could be identified in the corresponding locule walls. These data leave little doubt that the mutations in the cyst fluid are derived from the cyst locule walls and indicate that the cyst fluid provides an excellent representation of the neoplastic cells in an IPMN.

Example 5

GNAS Mutations in Invasive Cancers Associated with IPMNs

Prior whole exome sequencing had not revealed any GNAS mutations in 24 typical PDA that occurred in the absence of an associated IPMN (29). We extended these data by examining 95 additional surgically resected PDAs in pancreata without evidence of IPMNs for mutations in GNAS R201H or R201C, using the ligation assay described above. Again, no GNAS mutations were identified in PDAs arising in the absence of IPMNs.

We suspected that IPMNs containing GNAS mutations had the potential to progress to an invasive carcinoma because fluids from IPMNs with high-grade dysplasia contained such mutations (Table 1). However, in light of the multilocular and multifocal nature of IPMNs described above, it was not clear whether the cells of the locule(s) that progress to an invasive carcinoma were those that contained GNAS mutations. To address this question, we purified DNA from invasive pancreatic adenocarcinomas that developed in association with IPMNs. In each case, the neoplastic cells of the IPMN and of the invasive adenocarcinoma were carefully microdissected. In seven of the eight patients, the identical GNAS mutation found in the neoplastic cells of the IPMN was found in the concurrent invasive adenocarcinoma (FIG. 9 (Table S5)). The KRAS mutational status of the PDA was consistent with that of the associated IPMN in the same seven cases. In the eighth case, the KRAS and GNAS mutations identified in the neoplastic cells of the IPMN were not found in the associated PDA, suggesting that this invasive cancer arose from a separate precursor lesion (FIG. 9

(Table S5)). Though KRAS mutations were found commonly in both types of PDAs, there was a dramatic difference between the prevalence of GNAS mutations in PDAs associated with IPMNs (7 of 8) vs. that in PDAs unassociated with IPMNs (0 of 116; p<0.001, Fisher's Exact Test).

REFERENCES

The disclosure of each reference cited is expressly incorporated herein.
1. T. A. Laffan, K. M. Horton, A. P. Klein, B. Berlanstein, S. S. Siegelman, S. Kawamoto, P. T. Johnson, E. K. Fishman, R. H. Hruban, Prevalence of unsuspected pancreatic cysts on MDCT. AJR Am J Roentgenol 191, 802-807 (2008).
2. K. de Jong, C. Y. Nio, J. J. Hermans, M. G. Dijkgraaf, D. J. Gouma, C. H. J. van Eijck, E. van Heel, G. Klass, P. Fockens, M. J. Bruno, High Prevalence of Pancreatic Cysts Detected by Screening Magnetic Resonance Imaging Examinations. Clinical Gastroenterology and Hepatology 8, 806-811 (2010).
3. W. Kimura, H. Nagai, A. Kuroda, T. Muto, Y. Esaki, Analysis of small cystic lesions of the pancreas. Int J Pancreatol 18, 197-206 (1995).
4. K. S. Lee, A. Sekhar, N. M. Rofsky, I. Pedrosa, Prevalence of incidental pancreatic cysts in the adult population on MR imaging. Am J Gastroenterol 105, 2079-2084 (2010).
5. H. Matthaei, R. D. Schulick, R. H. Hruban, A. Maitra, Cystic precursors to invasive pancreatic cancer. Nature Reviews Gastroenterology & Hepatology 8, 141-150 (2011).
6. M. Katz, M. Mortenson, H. Wang, R. Hwang, E. Tamm, G. Staerkel, J. Lee, D. Evans, J. Fleming, Diagnosis and Management of Cystic Neoplasms of the Pancreas: An Evidence-Based Approach. Journal of the American College of Surgeons 207, 106-120 (2008).
7. M. Tanaka, Controversies in the management of pancreatic IPMN. Nature Reviews Gastroenterology & Hepatology 8, 56-60 (2011).
8. R. H. Hruban, M. B. Pitman, D. S. Klimstra, Tumors of the pancreas. Atlas of tumor pathology (American Registry of Pathology and Armed Forces Institute of Pathology, Washington, D.C., ed. Fourth Series, Fascicle 6, (2007).
9. G. Klöppel, M. Kosmahl, Cystic Lesions and Neoplasms of the Pancreas. Pancreatology 1, 8 (2001).
10. M. Tanaka, S. Chari, V. Adsay, C. Fernandez-del Castillo, M. Falconi, M. Shimizu, K. Yamaguchi, K. Yamao, S. Matsuno, International consensus guidelines for management of intraductal papillary mucinous neoplasms and mucinous cystic neoplasms of the pancreas. Pancreatology 6, 17-32 (2006).
11. T. A. Sohn, C. J. Yeo, J. L. Cameron, R. H. Hruban, N. Fukushima, K. A. Campbell, K. D. Lillemoe, Intraductal papillary mucinous neoplasms of the pancreas: an updated experience. Ann Surg 239, 788-797; discussion 797-789 (2004).
12. S. Crippa, C. Fernández-del Castillo, R. Salvia, D. Finkelstein, C. Bassi, I. Domínguez, A. Muzikansky, S. P. Thayer, M. Falconi, M. Mino-Kenudson, Mucin-Producing Neoplasms of the Pancreas: An Analysis of Distinguishing Clinical and Epidemiologic Characteristics. Clinical Gastroenterology and Hepatology 8, 213-219.e214 (2010).
13. G. A. Poultsides, S. Reddy, J. L. Cameron, R. H. Hruban, T. M. Pawlik, N. Ahuja, A. Jain, B. H. Edil, C. A. Iacobuzio-Donahue, R. D. Schulick, C. L. Wolfgang, Histopathologic basis for the favorable survival after resection of intraductal papillary mucinous neoplasm-associated invasive adenocarcinoma of the pancreas. Ann Surg 251, 470-476 (2010).
14. T. A. Sohn, C. J. Yeo, J. L. Cameron, L. Koniaris, S. Kaushal, R. A. Abrams, P. I. Sauter, J. Coleman, R. H. Hruban, K. D. Lillemoe, Resected adenocarcinoma of the pancreas 616 patients results, outcomes, and prognostic indicators. Journal of Gastrointestinal Surgery 4, 13 (2000).
15. R. Salvia, C. Fernandez-del Castillo, C. Bassi, S. P. Thayer, M. Falconi, W. Mantovani, P. Pederzoli, A. L. Warshaw, Main-duct intraductal papillary mucinous neoplasms of the pancreas: clinical predictors of malignancy and long-term survival following resection. Ann Surg 239, 678-685; discussion 685-677 (2004).
16. P. U. Freda, W. K. Chung, N. Matsuoka, J. E. Walsh, M. N. Kanibir, G. Kleinman, Y. Wang, J. N. Bruce, K. D. Post, Analysis of GNAS mutations in 60 growth hormone secreting pituitary tumors: correlation with clinical and pathological characteristics and surgical outcome based on highly sensitive GH and IGF-I criteria for remission. Pituitary 10, 275-282 (2007).
17. N. Kalfa, Activating Mutations of the Stimulatory G Protein in Juvenile Ovarian Granulosa Cell Tumors: A New Prognostic Factor? Journal of Clinical Endocrinology & Metabolism 91, 1842-1847 (2006).
18. M. C. Fragoso, A. C. Latronico, F. M. Carvalho, M. C. Zerbini, J. A. Marcondes, L. M. Araujo, V. S. Lando, E. T. Frazzatto, B. B. Mendonca, S. M. Villares, Activating mutation of the stimulatory G protein (gsp) as a putative cause of ovarian and testicular human stromal Leydig cell tumors. J Clin Endocrinol Metab 83, 2074-2078 (1998).
19. H. Yamasaki, N. Mizusawa, S. Nagahiro, S. Yamada, T. Sano, M. Itakura, K. Yoshimoto, GH-secreting pituitary adenomas infrequently contain inactivating mutations of PRKAR1A and LOH of 17q23-24. Clin Endocrinol (Oxf) 58, 464-470 (2003).
20. L. D. Wood, D. W. Parsons, S. Jones, J. Lin, T. Sjoblom, R. J. Leary, D. Shen, S. M. Boca, T. Barber, J. Ptak, N. Silliman, S. Szabo, Z. Derso, V. Ustyanksky, T. Nikolskaya, Y. Nikolsky, R. Karchin, P. A. Wilson, J. S. Kaminker, Z. Zhang, R. Croshaw, J. Willis, D. Dawson, M. Shipitsin, J. K. V. Willson, S. Sukumar, K. Polyak, B. H. Park, C. L. Pethiyagoda, P. V. K. Pant, D. G. Ballinger, A. B. Sparks, J. Hartigan, D. R. Smith, E. Suh, N. Papadopoulos, P. Buckhaults, S. D. Markowitz, G. Parmigiani, K. W. Kinzler, V. E. Velculescu, B. Vogelstein, The Genomic Landscapes of Human Breast and Colorectal Cancers. Science 318, 1108-1113 (2007).
21. S. Idziaszczyk, C. H. Wilson, C. G. Smith, D. J. Adams, J. P. Cheadle, Analysis of the frequency of GNAS codon 201 mutations in advanced colorectal cancer. Cancer Genetics and Cytogenetics 202, 67-69 (2010).
22. J.-S. Shin, A. Spillane, E. Wills, W. A. Cooper, PEComa of the retroperitoneum. Pathology 40, 93-95 (2008).
23. I. J. Dahabreh, T. Terasawa, P. J. Castaldi, T. A. Trikalinos, Systematic review: Anti-epidermal growth factor receptor treatment effect modification by KRAS mutations in advanced colorectal cancer. Ann Intern Med 154, 37-49 (2011).
24. C Almoguera, D. Shibata, K. Forrester, J. Martin, N. Arnheim, M. Perucho, Most human carcinomas of the exocrine pancreas contain mutant c-K-ras genes. Cell 53, 549-554 (1988).
25. S. Fritz, C. Fernandez-del Castillo, M. Mino-Kenudson, S. Crippa, V. Deshpande, G. Y. Lauwers, A. L. Warshaw, S. P. Thayer, A. J. Iafrate, Global Genomic Analysis of Intraductal Papillary Mucinous Neoplasms of the Pancreas Reveals Significant Molecular Differences Compared to Ductal Adenocarcinoma. Annals of Surgery 249, 440-447 (2009).

26. D. Soldini, M. Gugger, E. Burckhardt, A. Kappeler, J. A. Laissue, L. Mazzucchelli, Progressive genomic alterations in intraductal papillary mucinous tumours of the pancreas and morphologically similar lesions of the pancreatic ducts. The Journal of Pathology 199, 453-461 (2003).

27. F. Schonleben, W. Qiu, K. C. Bruckman, N. T. Ciau, X. Li, M. H. Lauerman, H. Frucht, J. A. Chabot, J. D. Allendorf, H. E. Remotti, BRAF and KRAS gene mutations in intraductal papillary mucinous neoplasm/carcinoma (IPMN/IPMC) of the pancreas. Cancer Letters 249, 242-248 (2007).

28. K. Wada, Does "clonal progression" relate to the development of intraductal papillary mucinous tumors of the pancreas? Journal of Gastrointestinal Surgery 8, 289-296 (2004).

29. S. Jones, X. Zhang, D. W. Parsons, J. C. H. Lin, R. J. Leary, P. Angenendt, P. Mankoo, H. Carter, H. Kamiyama, A. Jimeno, S. M. Hong, B. Fu, M. T. Lin, E. S. Calhoun, M. Kamiyama, K. Walter, T. Nikolskaya, Y. Nikolsky, J. Hartigan, D. R. Smith, M. Hidalgo, S. D. Leach, A. P. Klein, E. M. Jaffee, M. Goggins, A. Maitra, C. Iacobuzio-Donahue, J. R. Eshleman, S. E. Kern, R. H. Hruban, R. Karchin, N. Papadopoulos, G. Parmigiani, B. Vogelstein, V. E. Velculescu, K. W Kinzler, Core Signaling Pathways in Human Pancreatic Cancers Revealed by Global Genomic Analyses. Science 321, 1801-1806 (2008).

30. G. Parmigiani, S. Boca, J. Lin, K. W. Kinzler, V. Velculescu, B. Vogelstein, Design and analysis issues in genome-wide somatic mutation studies of cancer. Genomics 93, 17-21 (2009).

31. F. Schonleben, J. D. Allendorf, W. Qiu, X. Li, D. J. Ho, N. T. Ciau, R. L. Fine, J. A. Chabot, H. E. Remotti, G. H. Su, Mutational analyses of multiple oncogenic pathways in intraductal papillary mucinous neoplasms of the pancreas. Pancreas 36, 168-172 (2008).

32. M. Kitago, M. Ueda, K. Aiura, K. Suzuki, S. Hoshimoto, S. Takahashi, M. Mukai, M. Kitajima, Comparison of K-ras point mutation distributions in intraductal papillary-mucinous tumors and ductal adenocarcinoma of the pancreas. International Journal of Cancer 110, 177-182 (2004).

33. T. Izawa, T. Obara, S. Tanno, Y. Mizukami, N. Yanagawa, Y. Kohgo, Clonality and Field Cancerization in Intraductal Papillary-Mucinous Tumors of the Pancreas. Cancer 92, 11 (2001).

34. F. Diehl, M. Li, Y. He, K. W. Kinzler, B. Vogelstein, D. Dressman, BEAMing: single-molecule PCR on microparticles in water-in-oil emulsions. Nature Methods 3, 551-559 (2006).

35. H. Fujii, M. Inagaki, S. Kasai, N. Miyokawa, Y. Tokusashi, E. Gabrielson, R. H. Hruban, Genetic progression and heterogeneity in intraductal papillary-mucinous neoplasms of the pancreas. American Journal of Pathology 151, 8 (1997).

36. B. Taouli, V. r. Vilgrain, M.-P. Vullierme, B. t. Terris, A. Denys, A. Sauvanet, P. Hammel, Y. Menu, Intraductal Papillary Mucinous Tumors of the Pancreas: Helical CT with Histopathologic Correlation. Radiology 217, 8 (2000).

37. A. Diaz, M. Danon, J. Crawford, McCune-Albright syndrome and disorders due to activating mutations of GNAS1. J Pediatr Endocrinol Metab 20, 853-880 (2007).

38. A. Lania, A. Spada, G-protein and signalling in pituitary tumours. Horm Res 71 Suppl 2, 95-100 (2009).

39. A. G. Lania, G. Mantovani, A. Spada, Mechanisms of disease: Mutations of G proteins and G-protein-coupled receptors in endocrine diseases. Nat Clin Pract Endocrinol Metab 2, 681-693 (2006).

40. D. Shibata, J. Schaeffer, Z. H. Li, G. Capella, M. Perucho, Genetic heterogeneity of the c-K-ras locus in colorectal adenomas but not in adenocarcinomas. J Natl Cancer Inst 85, 1058-1063 (1993).

41. S. Jones, W. D. Chen, G. Parmigiani, F. Diehl, N. Beerenwinkel, T. Antal, A. Traulsen, M. A. Nowak, C. Siegel, V. E. Velculescu, K. W. Kinzler, B. Vogelstein, J. Willis, S. D. Markowitz, Comparative lesion sequencing provides insights into tumor evolution. Proc Natl Acad Sci USA 105, 4283-4288 (2008).

42. C. Correa-Gallego, C. R. Ferrone, S. P. Thayer, J. A. Wargo, A. L. Warshaw, C. Fernández-del Castillo, Incidental Pancreatic Cysts: Do We Really Know What We Are Watching? Pancreatology 10, 144-150 (2010).

43. J. F. Tseng, A. L. Warshaw, D. V. Sahani, G. Y. Lauwers, D. W. Rattner, C. F.-d. Castillo, Serous Cystadenoma of the Pancreas. Transactions of the . . . Meeting of the American Surgical Association 123, 111-118 (2005).

44. S.-M. Hong, D. Kelly, M. Griffith, N. Omura, A. Li, C.-P. Li, R. H. Hruban, M. Goggins, Multiple genes are hypermethylated in intraductal papillary mucinous neoplasms of the pancreas. Mod Pathol 21, 9 (2008).

45. P. J. Allen, L.-X. Qin, L. Tang, D. Klimstra, M. F. Brennan, A. Lokshin, Pancreatic Cyst Fluid Protein Expression Profiling for Discriminating Between Serous Cystadenoma and Intraductal Papillary Mucinous Neoplasm Annals of Surgery 250, 754-760 (2009).

46. E. Ke, B. B. Patel, T. Liu, X.-M. Li, O. Haluszka, J. P. Hoffman, H. Ehya, N. A. Young, J. C. Watson, D. S. Weinberg, M. T. Nguyen, S. J. Cohen, N. J. Meropol, S. Litwin, J. L. Tokar, A. T. Yeung, Proteomic Analyses of Pancreatic Cyst Fluids. Pancreas 38, 10 (2009).

47. A. Khalid, M. Zahid, S. D. Finkelstein, J. K. LeBlanc, N. Kaushik, N. Ahmad, W. R. Brugge, S. A. Edmundowicz, R. H. Hawes, K. M. McGrath, Pancreatic cyst fluid DNA analysis in evaluating pancreatic cysts: a report of the PANDA study. Gastrointest Endosc 69, 1095-1102 (2009).

48. M. S. Sawhney, S. Devarajan, P. O'Farrel, M. S. Cury, R. Kundu, C. M. Vollmer, A. Brown, R. Chuttani, D. K. Pleskow, Comparison of carcinoembryonic antigen and molecular analysis in pancreatic cyst fluid. Gastrointestinal Endoscopy 69, 1106-1110 (2009).

49. K. E. Schoedel, S. D. Finkelstein, N. P. Ohori, K-Ras and microsatellite marker analysis of fine-needle aspirates from intraductal papillary mucinous neoplasms of the pancreas. Diagnostic Cytopathology 34, 605-608 (2006).

50. D. Bartsch, D. Bastian, P. Barth, A. Schudy, C. Nies, O. Kisker, H. J. Wagner, M. Rothmund, K-ras oncogene mutations indicate malignancy in cystic tumors of the pancreas. Ann Surg 228, 79-86 (1998).

51. M. Al-Haddad, M. B. Wallace, T. A. Woodward, S. A. Gross, C. M. Hodgens, R. D. Toton, M. Raimondo, The safety of fine-needle aspiration guided by endoscopic ultrasound: a prospective study. Endoscopy 40, 204-208 (2008).

52. D. V. Sahani, R. Kadavigere, A. Saokar, C. Fernandez-del Castillo, W. R. Brugge, P. F. Hahn, Cystic pancreatic lesions: a simple imaging-based classification system for guiding management. Radiographics 25, 1471-1484 (2005).
53. F. T. Bosman, F. Carneiro, R. H. Hruban, N. D. Thiese, WHO Classification of Tumours of the Digestive system. (IARC Press, Lyon, ed. 4, 2010), vol. 3.
54. T. Furukawa, G. Kloppel, N. Volkan Adsay, J. Albores-Saavedra, N. Fukushima, A. Horii, R. H. Hruban, Y. Kato, D. S. Klimstra, D. S. Longnecker, J. Luttges, G. J. Offerhaus, M. Shimizu, M. Sunamura, A. Suriawinata, K. Takaori, S. Yonezawa, Classification of types of intraductal papillary-mucinous neoplasm of the pancreas: a consensus study. Virchows Arch 447, 794-799 (2005).
55. C. Rago, D. L. Huso, F. Diehl, B. Karim, G. Liu, N. Papadopoulos, Y. Samuels, V. E. Velculescu, B. Vogelstein, K. W. Kinzler, L. A. Diaz, Jr., Serial Assessment of Human Tumor Burdens in Mice by the Analysis of Circulating DNA. Cancer Res 67, 9364-9370 (2007).
56. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz Jr, Circulating mutant DNA to assess tumor dynamics Nature Medicine 14, 985-990 (2007).
57. D. S. Herman, G. K. Hovingh, O. Iartchouk, H. L. Rehm, R. Kucherlapati, J. G. Seidman, C. E. Seidman, Filter-based hybridization capture of subgenomes enables resequencing and copy-number detection. Nature Methods 6, 507-510 (2009).
58. C. Fouquet, M. Antoine, P. Tisserand, R. Favis, M. Wislez, F. Commo, N. Rabbe, M. F. Carette, B. Milleron, F. Barany, J. Cadranel, G. Zalcman, T. Soussi, Rapid and sensitive p53 alteration analysis in biopsies from lung cancer patients using a functional assay and a universal oligonucleotide array: a prospective study. Clin Cancer Res 10, 3479-3489 (2004).
59. S. M. Dong, G. Traverso, C. Johnson, L. Geng, R. Favis, K. Boynton, K. Hibi, S. N. Goodman, M. D'Allessio, P. Paty, S. R. Hamilton, D. Sidransky, F. Barany, B. Levin, A. Shuber, K. W Kinzler, B. Vogelstein, J. Jen, Detecting Colorectal Cancer in Stool With the Use of Multiple Genetic Targets. J Natl Cancer Inst 93, 858-865. (2001).
60. J. Luo, D. E. Bergstrom, F. Barany, Improving the fidelity of Thermus thermophilus DNA ligase. Nucleic Acids Res 24, 3071-3078 (1996).
61. C. Shi, S. H. Eshleman, D. Jones, N. Fukushima, L. Hua, A. R. Parker, C. J. Yeo, R. H. Hruban, M. G. Goggins, J. R. Eshleman, LigAmp for sensitive detection of single-nucleotide differences. Nat Methods 1, 141-147 (2004).
62. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz, Jr., Circulating mutant DNA to assess tumor dynamics Nat Med 14, 985-990 (2008).
63. T. S. L. StataCorp. 2009. Stata Statistical Software: Release 11. College Station.

The invention claimed is:

1. A method comprising the steps of:
   testing a sample comprising nucleic acids from pancreatic cyst fluid or pancreatic cyst wall tissue;
   detecting in the sample comprising nucleic acids a histidine or cysteine codon at codon 201 in GNAS;
   determining that the sample comprises a pancreatic intraductal papillary mucinous neoplasm (IPMN) when the histidine or cysteine codon is detected; and
   performing surgery to remove the IPMN.

2. The method of claim 1 further comprising the step of:
   detecting in the sample comprising nucleic acids an aspartic acid, valine, or arginine codon at codon 12 in KRAS.

3. The method of claim 1, wherein the sample is from pancreatic cyst fluid.

4. The method of claim 2, wherein the sample is from pancreatic cyst fluid.

5. The method of claim 1, wherein a histidine codon at codon 201 in GNAS is detected.

6. The method of claim 1, wherein a cysteine codon at codon 201 in GNAS is detected.

7. The method of claim 2, wherein an aspartic acid codon at codon 12 in KRAS is detected.

8. The method of claim 2, wherein a valine codon at codon 12 in KRAS is detected.

9. The method of claim 2, wherein a arginine codon at codon 12 in KRAS is detected.

10. The method of claim 1 wherein the sample is obtained by endoscopic ultrasound (EUS).

11. The method of claim 1 wherein:
    the sample is from pancreatic cyst wall tissue.

12. The method of claim 11, wherein a histidine codon at codon 201 in GNAS is detected.

13. The method of claim 11, wherein a cysteine codon at codon 201 in GNAS is detected.

14. The method of claim 11 wherein the sample is obtained by endoscopic ultrasound (EUS).

15. A method comprising the steps of:
    testing a sample comprising nucleic acids from pancreatic ductal adenocarcinoma tissue;
    detecting in the sample comprising nucleic acids a histidine or cysteine codon at codon 201 in GNAS; and
    performing surgery to remove the pancreatic ductal adenocarcinoma when the cysteine or histidine codon is detected.

16. The method of claim 15, wherein a histidine codon at codon 201 in GNAS is detected.

17. The method of claim 15, wherein a cysteine codon at codon 201 in GNAS is detected.

18. The method claim 15 wherein the sample is obtained by endoscopic ultrasound (EUS).

19. A method comprising the steps of:
    testing a sample comprising nucleic acids from a patient, wherein said sample is selected from the group consisting of pancreatic juice and stool;
    detecting in the sample comprising nucleic acids a cysteine or histidine codon at codon 201 in GNAS;
    determining that the patient has a pancreatic intraductal papillary mucinous neoplasm (IPMN) when the cysteine or histidine codon is detected; and
    performing surgery on the patient to remove the IPMN.

20. The method of claim 19 further comprising:
    detecting in the sample comprising nucleic acids an aspartic acid, valine, or arginine codon at codon 12 in KRAS.

21. The method of claim 19 further comprising:
    examining the patient to detect the presence of a pancreatic tumor.

22. The method of claim 20 further comprising:
    examining the patient to detect the presence of a pancreatic tumor.

* * * * *

UNITED STATES PATENT AND TRADEMARK OFFICE
CERTIFICATE OF CORRECTION

PATENT NO. : 9,976,184 B2  
APPLICATION NO. : 14/128478  
DATED : May 22, 2018  
INVENTOR(S) : Bert Vogelstein et al.

Page 1 of 1

It is certified that error appears in the above-identified patent and that said Letters Patent is hereby corrected as shown below:

On the Title Page (*) Column 1, Line 3: Delete "days. days." And insert --days.--, therefor.

In the Claims

Column 32, Line 29: Claim 18, after "method" insert --of--.

Signed and Sealed this  
Twenty-sixth Day of November, 2019

Andrei Iancu  
*Director of the United States Patent and Trademark Office*

UNITED STATES PATENT AND TRADEMARK OFFICE
CERTIFICATE OF CORRECTION

PATENT NO. : 9,976,184 B2
APPLICATION NO. : 14/128478
DATED : May 22, 2018
INVENTOR(S) : Bert Vogelstein et al.

Page 1 of 1

It is certified that error appears in the above-identified patent and that said Letters Patent is hereby corrected as shown below:

In the Specification

In Column 1 delete "This invention was made with funds from the United States government. The United States retains certain rights to the invention according to the terms of CA43460, CA 57345, and CA 62924." and insert --This invention was made with government support under CA043460, CA057345, and CA062924, awarded by the National Institutes of Health. The government has certain rights in the invention.--

Signed and Sealed this
Eighteenth Day of August, 2020

Andrei Iancu
*Director of the United States Patent and Trademark Office*